(12) United States Patent
Siiman et al.

(10) Patent No.: US 6,514,772 B2
(45) Date of Patent: Feb. 4, 2003

(54) SEMICONDUCTOR NANOPARTICLES FOR ANALYSIS OF BLOOD CELL POPULATIONS AND METHODS OF MAKING SAME

(75) Inventors: Olavi Siiman, Davie, FL (US); Egon Matijevic, Potsdam, NY (US); Ivan Sondi, Potsdam, NY (US)

(73) Assignee: Coulter International Corp., Miami, FL (US)

( * ) Notice: Subject to any disclaimer, the term of this patent is extended or adjusted under 35 U.S.C. 154(b) by 85 days.

(21) Appl. No.: 09/813,538

(22) Filed: May 8, 2001

(65) Prior Publication Data

US 2001/0039060 A1 Nov. 8, 2001

Related U.S. Application Data

(62) Division of application No. 09/281,512, filed on Mar. 30, 1999, now Pat. No. 6,235,540.

(51) Int. Cl.$^7$ ............................................. G01N 33/543
(52) U.S. Cl. ..................... 436/518; 427/2.13; 427/2.22; 427/212; 427/213.3; 427/215; 427/216; 427/220; 427/414; 428/402; 428/403; 436/524; 436/525; 436/529

(58) Field of Search ................................ 427/2.13, 2.22, 427/212, 213.3, 215, 216, 220, 414; 428/402, 403; 436/524, 525, 518, 529

(56) References Cited

U.S. PATENT DOCUMENTS

| | | | | |
|---|---|---|---|---|
| 5,248,772 A | * | 9/1993 | Siiman et al. | |
| 5,639,620 A | * | 6/1997 | Siiman et al. | |
| 5,707,877 A | * | 1/1998 | Siiman et al. | |
| 5,990,479 A | * | 11/1999 | Weiss et al. | |
| 6,114,038 A | * | 9/2000 | Castro | |

* cited by examiner

Primary Examiner—Christopher L. Chin
(74) Attorney, Agent, or Firm—Mitchell E. Alter

(57) ABSTRACT

A semiconductor nanoparticle for use in analysis of biological samples is described. This semiconductor nanoparticle is composed of an aminodextran which is bound to at least one nanoparticle of the formula $(X Y)_n$ wherein X is selected from the group comprising $Cd^{2+}$, $Hg^{2+}$, and $Zn^{2+}$ and combinations thereof, and Y is selected from the group comprising $S^{2-}$, $Se^{2-}$ and $Te^{2-}$ and combinations thereof; and n=approximately 50 to 1000. Also provided are methods of making these semiconductor nanoparticles and methods of making conjugates composed of these semiconductor nanoparticles linked to ligands. Also described are uses for the conjugates in a variety of biological assays.

5 Claims, 18 Drawing Sheets

SEMICONDUCTOR NANOPARTICLES FOR ANALYSIS OF BLOOD CELL POPULATIONS AND METHODS OF MAKING SAME

This application is a divisional of application Ser. No. 09/281,512 filed Mar 30, 1999 now U.S. Pat. No. 6,235,540.

FIELD OF THE INVENTION

The invention relates generally to methods of making semiconductor nanoparticle compounds useful in the analysis of blood cell populations, and particularly to compounds which contain amino-derivatized polysaccharides.

BACKGROUND OF THE INVENTION

Multiplex labeling of cells for analysis of biological samples, e.g., mixed cell populations, has been described. However, known methods have limitations which are dictated by the finite number of fluorescence emission colors of known organic fluorophores which can be squeezed into the visible, near-ultraviolet (UV), near-infrared (IR) spectral regions in which conventional measurements are made, e.g., by flow cytometry. These limitations include the widths of emission bands, the spectral overlap between these emission bands, and the excitation wavelength requirements.

Two examples of labels for cells are CdSe core nanoparticles which have been used for biological staining and observation with a fluorescence microscope [Bruchez J. M. et al., Science 281, 2013 (1998) and Chan, W. C. W. and Nie, S., Science 281, 2016 (1998)].

As the upper limit in the number of usable colors was reached, other methods, based on fluorescence intensity differences have been developed. For example, mutually exclusive pairs of targeted white blood cell populations with widely different, intrinsic numbers of receptors per cell can be labeled by a single color marker and analyzed by flow cytometry [U.S. Pat. No. 5,538,855].

Several non-radioactive gene probes, oligos with attached fluorescent dye that hybridize or bind to sample DNA have been described [L. M. Smith et al., Nature, 321:674–679 (1986) and L. M. Smith et al, Nucl. Acids Res., 13:2399–2412 (1985)] and are being used for labeling of biological samples. Automated DNA sequencers use four fluorescent dyes with non-overlapping emission bands, one per nucleotide base. However, electrophoretic mobilities of the fluorescent dye-oligo primer conjugates need to be similar for all four conjugates. Also the molecular weight of the conjugates cannot be too high, otherwise they will not move through the polyacrylamide or agarose gel used in the electrophoresis.

The need for increased sensitivity of probes used in automated analysis by attaching multiple marker molecules per oligonucleotide primer were recognized as early as 1986 [L. M. Smith et al, cited above]. However, only a limited degree of fluorescence enhancement has been possible for dye-oligo conjugates that are constrained to low molecular weight for separation by gel electrophoresis.

Aminodextrans have been used as reducing and/or protective agents in the preparation or coating of monodispersed colloidal dispersions of magnetic ferrite [U.S. Pat. No. 5,240,640], metal [U.S. Pat. No. 5,248,772], polystyrene [U.S. Pat. No. 5,466,609; U.S. Pat. No. 5,707,877; U.S. Pat. No. 5,639,620; U.S. Pat. No. 5,776,706], and polystyrene-metal [U.S. Pat. No. 5,552,086; U.S. Pat. No. 5,527,713] particles. Aminodextran of sufficiently large molecular weight can accommodate multiple protein molecules. Complexes containing such aminodextrans conjugated to a ligand and a selected fluorescent marker or label have been described. [See, Smith, C., et al, "Detection of Low-Density Surface Markers Using Novel Amplified Fluorochrome-Conjugated Antibodies", Cytometry, Suppl. 9, p. 56, presented at XIX Congress of International Society for Analytical Cytology, Mar. 3–7, 1998; R. Mylvaganam, et al., "Seven Markers, Four Colors, Single Laser Flow Cytometry Using Amplified Fluorochrome Conjugated Antibodies", Cytometry, Suppl. 9, p. 117 (1998), as presented at XIX Congress of International Society for Analytical Cytology, Mar. 3–7, 1998.] However, there continues to be a need for probes which permit increased assay sensitivity, by providing narrower fluorescence bandwidths and enhanced intensities, decreased probe size and increased probe stability.

SUMMARY OF THE INVENTION

The present invention advantageously provides particles which are of a smaller size than previously described labeled aminodextran complexes. The nanoparticles of the invention are further coated with an aminodextran of high degree of substitution to provide higher luminescence intensity than was previously possible in a single small particle.

Thus, in one aspect, the present invention provides a semiconductor nanoparticle for the analysis of fluid samples. The semiconductor nanoparticle contains a water soluble amino derivative of a polysaccharide having a molecular weight from approximately 3,000 to 3,000,000 Da, a size in diameter of less than approximately 150 nanometers, and a degree of substitution of total number of primary and secondary amino groups in the polysaccharide molecule ranging from 1/150 to 4/1. To form the semiconductor nanoparticle, this aminopolysaccharide is linked to at least one nanoparticle of the formula:

wherein X is selected from the group comprising $Cd^{2+}$, $Hg^{2+}$, and $Zn^{2+}$ and combinations thereof; and Y is selected from the group comprising $S^{2-}$, $Se^{2-}$ and $Te^{2-}$ and combinations thereof; and n=approximately 50 to 1000.

In another aspect, the present invention provides a semiconductor nanoparticle useful for the analysis of biological samples which is bound to an aminodextran having a molecular weight from approximately 3,000 to 500,000 Da, has a size in diameter of 2 to about 10 nanometers, and a degree of substitution of total number of primary and secondary amino groups in the dextran molecule ranging from 1/150 to 4/1. The aminodextran is covalently bound to at least one nanoparticle, which is defined as above.

In yet another aspect, the present invention provides a method of making a semiconductor nanoparticle. This method involves the steps of reacting an amino derivative of a polysaccharide having a molecular weight from approximately 3,000 to 3,000,000 Da with a Periodic Table Group IIB water soluble salt and a Group VIA salt to form a semiconductor nanoparticle. In this method, the semiconductor nanoparticle is a complex of the amino derivative of a polysaccharide and a nanoparticle. The aminopolysaccharide has a diameter of less than approximately 150 nanometers and a degree of substitution of total number of primary and secondary amino groups in the polysaccharide molecule ranging from 1/150 to 4/1. The Group IIB salt having a cation selected from the group consisting of $Cd^{2+}$, $Hg^{2+}$, and $Zn^{2+}$ and combinations thereof, and an anion selected from the group consisting Cl$^-$, ClO$_4^-$, NO$_3^-$ and SO$_4^{2-}$; said Group VIA water soluble salt having a cation selected from the group consisting of Li$^+$, Na$^+$, K$^+$, Rb$^+$, Cs$^+$, Sr$^{2+}$, and Ba$^{2+}$ and an anion selected from the group consisting of S$^{2-}$, Se$^{2-}$ and Te$^{2-}$ and combinations thereof; such that the anion selected for the Group IIB salt does not precipitate with the cation of the Group VIA salt. In this method, the presence of the reducing sugar in the polysaccharide retards photo-oxidation of the nanoparticle in the formed polysaccharide semiconductor nanoparticle complex.

In yet a further aspect, the present invention provides a method of making a semiconductor nanoparticle useful in the analysis of biological samples. This method involves mixing an amino derivative of a polysaccharide having a molecular weight from approximately 3,000,000 Da, has a size in diameter of less than approximately 150 nanometers, and a degree of substitution of total number of primary and secondary amino groups in the polysaccharide molecule ranging from 1/150 to 4/1, a water soluble first salt having a cation selected from the group consisting of Cd$^{2+}$, Hg$^{2+}$, and Zn$^{2+}$ and combinations thereof, and an anion selected from the group consisting Cl$^-$, ClO$_4^-$, NO$_3^-$ and SO$_4^{2-}$, and a water soluble second salt having a cation selected from the group consisting of Li$^+$, Na$^+$, K$^+$, Rb$^+$, Cs$^+$, Sr$^{2+}$, and Ba$^{2+}$ and an anion selected from the group consisting of S$^{2-}$, Se$^{2-}$ and Te$^{2-}$ and combinations thereof, such that the anion selected for the first salt does not precipitate with the cation of the second salt. Upon this mixing step, the first and second salts and the aminopolysaccharide react to form a semiconductor nanoparticle.

In yet a further aspect, the invention provides an aminopolysaccharide-semiconductor nanoparticle complex prepared according to a method of the invention. The semiconductor nanoparticle is a complex of the amino derivative of a polysaccharide and a nanoparticle.

In another aspect, the invention provides a ligand-semiconductor nanoparticle which contains a ligand conjugated to at least one semiconductor nanoparticle.

In still another aspect, the invention provides a method of preparing a ligand-semiconductor nanoparticle. The method involves mixing an amino derivative of a polysaccharide, a water soluble first salt, and a water soluble second salt to form a dispersion containing semiconductor nanoparticles. The dispersion is then purified to remove free salts, and the semiconductor nanoparticle is thereafter activated and purified. A ligand is separately activated and purified. The activated and purified ligand and semiconductor nanoparticle are then mixed, permitting formation of the ligand-semiconductor nanoparticle. The ligand-semiconductor nanoparticle is a conjugate between the selected ligand and the semiconductor nanoparticle.

In yet another aspect, the invention provides a method of detecting a target in a biological sample. The method involves contacting a biological sample suspected of containing a target for a selected ligand with a ligand-semiconductor nanoparticle of the present invention, exciting bound semiconductor nanoparticles to cause them to luminesce; and detecting the luminescence signal, thereby detecting the presence of the target in the sample.

Other aspects and advantages of the invention will be readily apparent from the detailed description of the invention.

DETAILED DESCRIPTION OF THE INVENTION

Figure 1:
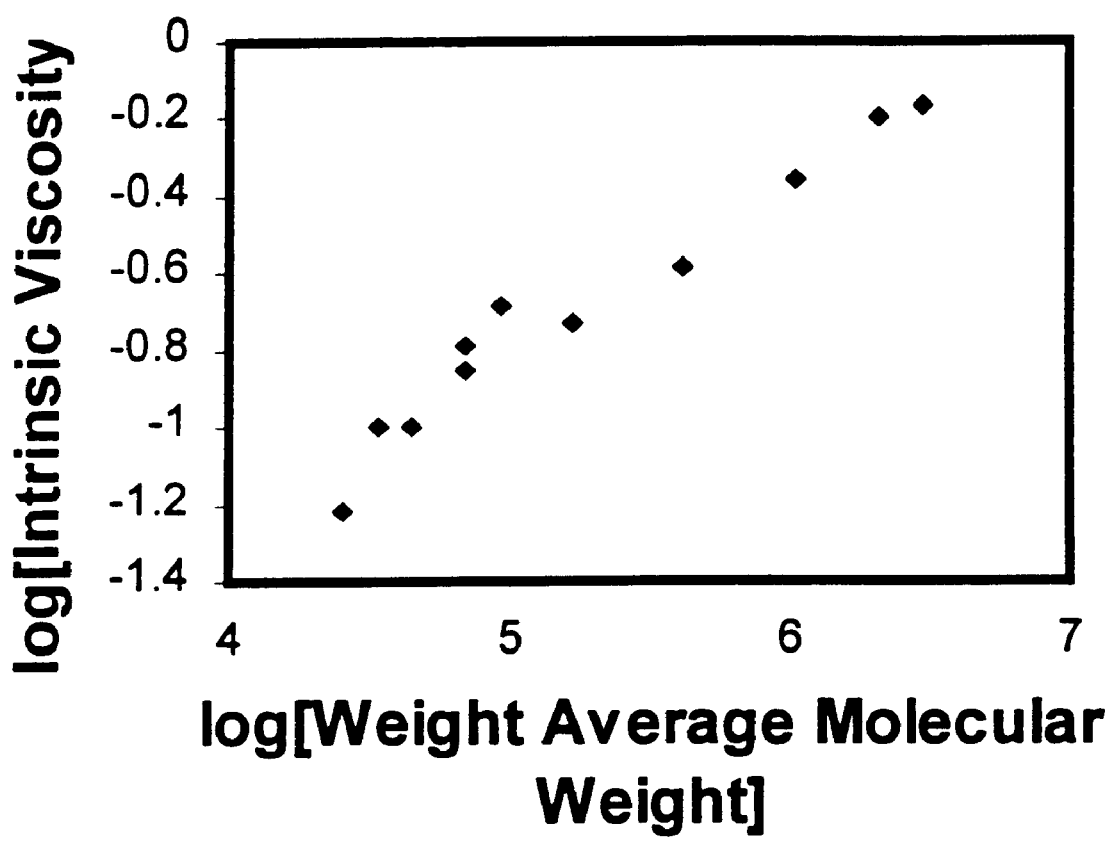
FIG. 1 provides the Mark-Houwink plot constructed from data for one dextran and ten aminodextran samples as listed in Table 1.

The present invention provides semiconductor nanoparticles which are useful in a variety of applications, but which are particularly well suited for use in biological assays. While previous attempts have been made to utilize amino-derived polysaccharide-particle conjugates for detection of a desired biological target, e.g., a subpopulation of white blood cells, the usefulness of these reagents has been limited to induction of light scattering shifts with relatively large particles. The semiconductor nanoparticles of the invention provide narrow luminescence bandwidths and the possibility of using nanoparticles of the same composition with at least three different sizes, each with different non-overlapping emission bands.

I. Semiconductor Nanoparticles

The semiconductor nanoparticles of the invention are composed of a water soluble amino derivative of a polysaccharide which is associated with at least one nanoparticle.

As defined herein, a polysaccharide useful in the invention has a molecular weight in the range from about 3,000 to 3,000,000 Da, from about 5000 to about 1,000,000, from about 10,000 to about 500,000, or from about 20,000 to about 250,000. This molecular weight may be readily measured by light scattering or the triple combination of light scattering, viscosity, and refractive index used for amino-dextrans (vide infra). Alternatively, other suitable means of determining molecular weight may be size exclusion chromatography or gel electrophoresis. The polysaccharide is also characterized by a size in diameter of about 1 to less than about 150 nanometers (nm) or about 10 to about 100 nm. Currently, a preferred size is in the range of about 10 to about 100 nanometers. In a currently preferred embodiment, the polysaccharide is dextran. However, other suitable polysaccharides may be readily selected by one of skill in the art. For example, such polysaccharides may be natural or synthetic, starches or starch derivatives, cellulose derivatives, amylose and pectin, as well as certain natural gums and derivatives thereof, such as gum arabic and salts of alginic acid.

The polysaccharide selected for use in the present invention is modified so as to contain a degree of substitution of total number of primary and secondary amino groups in the polysaccharide molecule ranging from 1/150 to 4/1 or from 1/25 to 2/5, while retaining water solubility up to at least 100 mg/mL. Unless otherwise noted, as used herein, the degree of substitution is the total number of amino groups (primary and secondary) per monomeric glucose unit in the amino-dextran or other aminopolysaccharide molecule. In a currently preferred embodiment the amino derivative of a polysaccharide used in the invention is aminodextran, most preferably which has been substituted with 1,3-diaminopropane. There are a variety of other aminodextrans which may be obtained from commercial sources or prepared using known techniques. Methods of preparing aminodextrans are described in U.S. Pat. No. 5,466,609 and U.S. Pat. No. 5,527,713 by periodate oxidation of dextran followed by reaction with 1,3-propanediamine. Of course, the present invention is not limited to these methods of producing aminodextrans. Preferably, the aminodextran is 5X-aminodextran (up to 350,000 Da, degree of substitution $1/5$–$1/8$, calculated on basis of primary amines) or 1X-aminodextran (up to 1,000,000 Da, degree of substitution, $1/28$–$1/45$, calculated on basis of primary amines). One of skill in the art may readily select other suitable aminodextrans and/or amino derivatives of polysaccharides for use in the present invention. The aminopolysaccharides are further characterized by having free amine groups which can be activated for linkage to a protein or other ligand.

The selected aminopolysaccharides are thereafter linked to at least one nanoparticle of the formula:

$$(XY)_n$$

wherein X is selected from the group comprising $Cd^{2+}$, $Hg^{2+}$, and $Zn^{2+}$ and combinations thereof; and Y is selected from the group comprising $S^{2-}$, $Se^{2-}$ and $Te^{2-}$ and combinations thereof; and n=approximately 50 to 1000. In a currently preferred embodiment, the nanoparticle is CdS.

In the semiconductor nanoparticle of the invention, each aminopolysaccharide may be covalently bound to one or more nanoparticles, and in certain embodiments, as many as several hundred nanoparticles (e.g., about 200) may be covalently bound to the aminopolysaccharide. The presence of luminescence in the resulting semiconductor nanoparticles is believed to be an indication of covalent binding.

II. Method of Making Semiconductor Nanoparticles

In another aspect, the present invention provides methods of making the semiconductor nanoparticles of the invention.

This method involves reacting an aminopolysaccharide as defined herein, a cation from Group IIB of the Periodic Table selected from among one or more of $Cd^{2+}$, $Hg^{2+}$, and $Zn^{2+}$, and an anion from Group VIA of the Periodic Table selected from among one or more of $S^{2-}$, $Se^{2-}$ and $Te^{2-}$.

Suitably, the cation donor is water soluble at room temperature. In a preferred embodiment, the cation donor is a Group IIB salt in which the cation is selected from among $Cd^{2+}$, $Hg^{2+}$, and $Zn^{2+}$ and combinations thereof; and the anion is selected from among $Cl^-$, $ClO_4^-$, $NO_3^-$ and $SO_4^{2-}$. Currently, the preferred cation is $Cd^{2+}$. Thus, examples of suitable Group IIB salts include $CdCl_2$, $Cd(ClO_4)_2$, $Cd(NO_3)_2$ and $CdSO_4$. Suitably, these salts may be in solution, or provided in dry form.

Suitably, the anion donor is also water soluble at room temperature. Preferably, the anion donor is a Group VIA salt or salt solution which has a cation selected from among $Li^+$, $Na^+$, $K^+$, $Rb^+$, $Cs^+$, $Sr^{2+}$, and $Ba^{2+}$ and an anion selected from among $S^{2-}$, $Se^{2-}$ and $Te^{2-}$ and combinations thereof The Group IIB salt and the Group VIA salt are selected so that the anion of the Group IIB salt does not precipitate with the cation of the Group VIA salt and the cation of the Group VIA salt does not precipitate with hydroxide ion. This determination is well within the skill of those in the art. Currently, the preferred anion is $S^{2-}$. Thus, examples of suitable Group VIA salts include $Li_2S$, $Na_2S$, $K_2S$, $Rb_2S$, $Cs_2S$, SrS, and BaS. Suitably, these salts may be in solution, or provided in dry form.

Desirably, the aminopolysaccharide is mixed in aqueous media which contain, at a minimum water, with the cation donor and the anion donor. The mixture containing the aminopolysaccharide, the Group IIB cation donor and the Group VIA anion donor are then reacted to form polysaccharide semiconductor nanoparticles.

In one embodiment, the cation donor (e.g., Group IIB salt) is mixed with the aminopolysaccharide to form a first product and the anion donor (e.g., Group VIA salt) is mixed with the aminopolysaccharide to form a second product. The first product and the second product are then reacted to form the polysaccharide semiconductor complex. Suitably, this occurs in the presence of a high concentration of aminopolysaccharide. The aminopolysaccharide may be added in high concentration before addition of the cation and/or anion donors (e.g., salts). Alternatively, aminopolysaccharide may be added during the mixing process substantially simultaneously with or before addition of the salt(s). As defined herein, "high concentration" of aminopolysaccharide refers to an amount in the range of 0.2 to about 50 mg aminopolysaccharide per ml of reaction mixture, preferably, about 15 mg/ml to about 25 mg/ml, and more preferably about 20 mg/ml aminopolysaccharide/reaction mixture.

The Group IIB cation and the Group VIA anion may be added to the water in approximately equivalent amounts (i.e., at a molar ratio of about 1 to about 1). For example, Group IIB salts and Group VIA salts may be added in amounts so that the mixture contains about $1 \times 10^{-4}$ mol $dm^{-3}$ to $1 \times 10^{-1}$ mol $dm^{-3}$. However, to obtain maximum luminescence emission intensity from the nanoparticles, superior results have been obtained when the mixture contains an excess of the donated cation from the Group IIB salt, as compared to the concentration of the anion from the Group VIA salt. This excess donated cation may be as much as about 50% higher concentration of the Group IIB salt. However, this is believed to reflect optimization of the present invention and is not essential for production of the semiconductor nanoparticles of the invention.

Suitably, the method of the invention is performed at a relatively high pH, e.g., in the range of about 9 to about 12, and most suitably, in the range of about 10 to 11. Where needed, the pH may be adjusted by addition of a water soluble base, e.g., NaOH, to the reaction mixture. One of skill in the art can readily select other suitable water-soluble bases such as KOH, NaOH, LiOH, RbOH, CsOH, $Sr(OH)_2$, or $Ba(OH)_2$ for use in the method of the invention.

In one desirable embodiment, the semiconductor nanoparticles of the invention are prepared by rapid mixing of reactant solutions. Generally, this procedure involves rapidly adding a Group IIB salt solution into a stirred solution of a Group VIA salt containing aminodextran. The mixing of these solutions yields sols of Group IIB cation/Group VIA anion. These sols are then further stirred. The pH is raised with NaOH to about 10–11. This rapid mixing invention has been found to yield semiconductor nanoparticles of a consistently smaller size than those produced by other methods.

Alternatively, the semiconductor nanoparticles of the invention may be prepared using a controlled double-jet precipitation process. Generally, this method involves introducing solutions containing the Group IIB salt and the Group VIA salt into a reactor containing stirred aqueous aminopolysaccharide solution. The reactor outer jacket is suitably maintained at a temperature which prevents overheating (e.g., about 25° C.). The mixing immediately yields sols, which are further stirred. Suitably, the pH of the prepared semiconductor nanoparticle dispersions is adjusted to a pH of about 10–11, and most preferably 10.5. This controlled double-jet precipitation process has been found to yield a more stable dispersion of semiconductor nanoparticles of the invention than when it is prepared by the rapid mixing method, particularly at high concentrations.

Regardless of whether these mixing processes or other mixing processes are selected by one of skill in the art for use in the method of the invention, it has been found that there are sufficient amounts of reducing sugars in the aminopolysaccharide that photo-oxidation of the formed aminopolysaccharide semiconductor nanoparticle is retarded, and no further steps are required to prevent photo-oxidation. Thus, the dispersion resulting from the above-described reaction contains stable, fluorescent, semiconductor nanoparticles.

Suitably, the resulting dispersion of luminescent semiconductor nanoparticles is characterized by an emission spectrum which is dependent upon the elements which form the nanoparticle, the size of the resulting semiconductor nanoparticle, and the concentration of the semiconductor nanoparticle in the dispersion. Suitably, each type of semiconductor nanoparticle, e.g., such as CdS-aminodextran, can provide at least three non-overlapping emission bands, through the use of different nanoparticle sizes between 2 and 10 nm in diameter. For example, CdS dispersions may give luminescence band maxima from 450 nm for low concentrations of aminodextran to 550 nm at the highest concentration. Other types of II-VI semiconductors, either singly or in combination from the following array, may be readily selected for use in the method of the invention.

| Matrix of II–VI Semiconductors | | | |
| --- | --- | --- | --- |
|  | $Zn^{2+}$ | $Cd^{2+}$ | $Hg^{2+}$ |
| $S^{2-}$ | ZnS | CdS | HgS |
| $Se^{2-}$ | ZnSe | CdSe | HgSe |
| $Te^{2-}$ | ZnTe | CdTe | HgTe |

Generally, the emission spectra of the II-VI semiconductors which compose these nanoparticles span the range from blue (~450 nm) to red (~900 nm). These spectra can be readily determined by one of skill in the art using conventional methods. Suitably, the semiconductor nanoparticles of the invention may be used singly or in combination as mixed nanoparticles with other types of semiconductors to provide continuous tunability of emission bands from blue to red wavelengths. Selection of the desired nanoparticles, taking into consideration emission spectra, may depend upon the desired use for these semiconductor nanoparticles. Desirably, these semiconductor nanoparticles are purified prior to conjugation with a ligand, as described in detail below, or used in a variety of other applications.

Purification may be performed by any suitable means known in the art. Currently, a particularly desirable method is chromatography, e.g., using a Sephadex or Bio-Gel column. However, other suitable methods of purification such as membrane filtration may be readily selected.

III. A Ligand-Aminopolysaccharide-Semiconductor Nanoparticle Conjugate

Suitably, the semiconductor nanoparticle-aminopolysaccharide complexes of the invention may be linked to a protein or other ligand for use as markers, in biological assays, and the like.

As defined herein, the term "ligand" refers to a component which preferentially binds to all or a portion of a target peptide or protein. Preferably, this target is a viral or cell surface receptor or other protein and a ligand useful in the invention is an antibody or a functional fragment thereof (i.e., a fragment which binds the same target as the antibody) specific for the target protein Such antibodies or fragments include polyclonal antibodies from any native source, and native or recombinant monoclonal antibodies of classes IgG, IgM, IgA, IgD, and IgE, hybrid derivatives, and fragments of antibodies including Fab, Fab' and F(ab')$_2$, humanized or human antibodies, recombinant or synthetic constructs containing the complementarity determining regions of an antibody, and the like. Most preferably, a ligand useful in this invention is capable of binding to a cell surface receptor on a population of white blood cells (WBC). For use in detecting WBC populations, a preferred ligand is an anti-CD4 antibody. The methods useful for construction of all such ligands are known to those of skill in the art. The particular method of making and the type of monoclonal antibody is not limited to such techniques and it is envisioned that any technique for making such antibodies is within the practice of the invention Similarly, the selection of the ligand or target protein is not a limiting factor in this invention.

IV. A Method of Preparing a Ligand-Aminopolysaccharide-Semiconductor Nanoparticle Conjugate Thus, in another aspect, the present invention provides a method of preparing a ligand-aminopolysaccharide semiconductor nanoparticle conjugate. Suitably, this method involves activating a purified semiconductor nanoparticle-aminodextran complex of the invention using conventional methods. For example, activation may be by addition of sulfosuccinimidyl 4-[N-maleimidomethyl]cyclohexane-1-carboxylate (sulfo-SMCC) solution in 1×PBS to the dispersion containing the purified semiconductor nanoparticle-aminodextran complex. The activated semiconductor nanoparticle-aminodextran complex is then purified. Suitable purification methods may be readily selected by one of skill in the art. In one example, the mixture containing sulfo-SMCC and semiconductor nanoparticle-aminodextran complex are stirred (e.g., for about one hour at room temperature) and the reaction mixture chromatographed, e.g., by application of the mixture to a G-50 Sephadex column equilibrated with 1×PBS. A sample may then be eluted using 1×PBS, collected, and absorption determined to confirm activation. Other suitable activation and purification methods may be readily determined and substituted for the above-described method.

The selected ligand, i.e., a monoclonal antibody, is also activated. Suitable activation methods may be readily selected by one skill in the art. An example of such a method involves the addition of a solution of 2-iminothiolane in 1×PBS to antibody concentrate. The resulting solution suitably has an iminothiolane-to-antibody molar activation ratio of about 5–20 and preferably from 10–15 and is mixed at ambient temperature for about one to two hours. The activated antibody is then purified, e.g., by chromatography or another suitable method, and combined with the activated and purified polysaccharide-semiconductor nanoparticle complex.

Suitably, the dispersion containing the activated, purified ligand and the activated, purified polysaccharide-semiconductor nanoparticle complex or mixtures thereof is stirred for a sufficient time to permit formation of the ligand-polysaccharide-semiconductor nanoparticle conjugate.

The ratio of ligand to polysaccharide-semiconductor nanoparticle complex in the resulting conjugate will depend upon a number of factors, including the relative sizes of the polysaccharide-semiconductor nanoparticle complex and the ligand. For example, a conjugate of the invention composed of an antibody and an aminodextran-CdS semiconductor particle may contain about 5 to about 8 antibodies to each aminodextran-CdS semiconductor particle. However, other conjugates may contain a ratio of 1 ligand to each semiconductor nanoparticle, or may even contain as many as five polysaccharide-semiconductor nanoparticles to each antibody. Suitably, the number of polysaccharide-semiconductor nanoparticles complexed to the ligand is such that the activity of the ligand is not substantially affected.

So formed, the conjugates may be used in a wide variety of ways. For example, for enhancing known methodologies for the detection, diagnosis, measurement and study of antigens and other proteins, either present as individual molecules or in more complex organizations, such as viruses, cells, tissue, organelles, e.g., plasmids, nuclei, etc. The conjugates may be used in immunoassays or competitive protein binding assays, where the semiconductor particles serve as fluorescent labels.

V. A Method of Detecting a Target in a Biological Sample

According to the present invention, a particularly desirable use of the subject conjugates is labeling (i.e., luminescent staining) of cells. These conjugates may be used as single markers which provide an enhanced signal. In another embodiment the conjugates may be used in combinations, preferably where the luminescence emission maximum of the ligand-aminopolysaccharide-semiconductor nanoparticle conjugates are separated by at least about 50 nm, preferably by at least about 70 nm. Alternatively, the conjugates may be used in conjunction with other protein or non-protein fluorophores, where the emission maxima are separated by at least about 100 nm, preferably about 150 nm.

By using combinations of fluorophores, one can provide for the detection of subsets of aggregations, such as particular types of cells, strains of organisms, strains of viruses, the natural complexing or interaction of different proteins or antigens, etc. In some embodiments, combinations include fluorophores capable of being excited with the same laser light source.

Thus, according to this invention, cell populations may be identified by using one or more of: (a) a semiconductor nanoparticle conjugate of the invention containing a ligand (e.g., an antibody which binds a cell surface antigenic receptor) on a first cell subpopulation; and (b) a second semiconductor nanoparticle conjugate of the invention having a different wavelength of luminescence emission than the first conjugate due to either a sufficiently different nanoparticle size or nanoparticle composition and an antibody specific for a mutually exclusive second cell subpopulation. Optionally, the cell population may be identified using a conventional labeled conjugate in addition to a semiconductor nanoparticle conjugate(s) of the invention. The combination of these labeled, receptor-bound conjugates produces different luminescent-labeled cell populations in mixtures with whole blood with distinct and non-overlapping luminescence band maximum positions. Viruses and other biological targets may be identified using similar techniques.

The conjugates of the invention are particularly well suited for detecting a target in a biological sample. Typically, this involves contacting a biological sample suspecting of containing a target for a selected ligand with the ligand-semiconductor nanoparticle conjugate, exciting bound semiconductor nanoparticle conjugate to cause it to luminesce; and detecting the luminescence signal which is indicative of the presence of the target in the sample. This method is particularly well suited to flow cytometry analysis.

However, other methods, including enzyme linked immunosorbent assay (ELISA) may be readily utilized. In ELISA, or another similar method, the biological sample, or the conjugate may be immobilized. Where this is the case, a washing step may be employed to separate the semiconductor nanoparticle conjugate which has bound to the target from unbound semiconductor nanoparticle conjugate.

In one particularly desirable embodiment, the method of the invention is employed to detect multiple subsets of white blood cells. In this application, one to multiple sets of WBC cell populations are provided. For the first population, a first ligand-semiconductor nanoparticle conjugate of the invention is provided, in which the ligand binds to a receptor in the first population. For the second population, a second labeled ligand is provided. The second ligand binds to a second receptor within the population of white blood cells and is provided with a label which is distinguishable (e.g., visually or colorimetrically) from the semiconductor nanoparticle conjugate conjugated to the first ligand. This second ligand may be conjugated to a second semiconductor nanoparticle conjugate or to a conventional label. The cell populations are then incubated with the first and the second labeled ligands for a time sufficient to permit receptor-labeled ligand complexes to form therebetween. Where semiconductor nanoparticles have been utilized as the labels, the luminescence emission intensities may be determined and the populations distinguished by the variations in intensity and color.

Other suitable assays and uses for the semiconductor nanoparticle conjugates of the invention may be readily determined by one of skill in the art.

The following examples are provided to illustrative only and do not limit the scope of the invention. One skilled in the art will appreciate that although specific reagents and conditions are outlined in the following examples, modifications can be made which are meant to be encompassed by the spirit and scope of the invention.

EXAMPLE 1

Preparation of Aminodextrans

Aminodextran-3M and -3000 were obtained from Molecular Probes, Inc., Eugene, Oreg. Dextran, amino, nominally of 2,000,000 MW, Cat. No. D-7145, was purchased from Molecular Probes, Inc., Eugene, Oreg. Analytical data for lot 6551-3: 130 amines/mole. Measurement of the molecular weight of this lot of aminodextran by the Viscotek triple detection system (vide infra) gave ~3M Da. Therefore, there are 3,000,000 g/mol÷162.1 g/mol glucose monomer=18,507 glucose units/dextran molecule or 130/18,507=0.00702, i.e. ~1/142 degree of substitution with single amine group per reacted glucose unit. The degree of substitution unless otherwise noted is defined as the total number of amino groups (primary and secondary) per monomeric glucose unit in the aminodextran molecule. Dextrans of different average molecular weights (20,000 Da and 500,000 Da) were obtained from the Fluka Company.

Dextran, T-2M, for the preparation of aminodextrans was obtained from Sigma, as were other chemicals related to their preparation. All inorganic chemicals were of reagent grade and were not further purified.

1. Preparation of 1x-aminodextran and 5x-aminodextran.

The 1x-aminodextran and 5x-aminodextran lots were prepared as follows. In a standard preparation of 1X-Amdex, 80 g of solid dextran were blended in 600 mL distilled water to dissolve all the dextran. 8.56 g of sodium m-periodate, dissolved in 100 mL of distilled water, were added dropwise to the dextran solution over about 10 minutes with vigorous stirring, after which the mixture was stirred at room temperature for an additional 3 hours. The resulting viscous reaction mixture was then diluted to 2 liters with distilled water and desalted using a hollow fiber cartridge, A/G Technology Corp. model UFP-5-E-35, 5,000 molecular weight cut-off or model UFP-30-E-35, 30,000 molecular weight cut-off, with tubing adaptor kit, KA12-3P. About 18–22 L of distilled water were used to obtain a solution having a final pH of 6.0–6.5. To the final, 800 mL volume of washed, oxidized dextran solution were slowly added 80 mL of colorless, liquid 1,3-diaminopropane (DAP), over about 10 minutes at room temperature. The resulting mixture was then stirred at room temperature for an additional 3 hours. Then, 3.2 g of sodium borohydride dissolved in 40 mL of 1 mM aqueous sodium hydroxide were added to the room temperature aminodextran reaction mixture over about 5 minutes with stirring. The resulting mixture was stirred for an additional 1 hour and then desalted using a hollow fiber cartridge. About 20–25 L of distilled water were needed to reduce the specific conductance to about 3–4 $\mu$mho-cm$^{-1}$ and the pH to 6.0–6.5. The final volume of aminodextran was 400 mL. This solution was passed through a 0.2 $\mu$m sterile cellulose acetate filter unit and then freeze-dried over 48 hours in a model TDS-00030-A, Dura-Dry microprocessor-controlled freeze-drier (FTS Systems, Inc.) to obtain 48 grams of flaky, pale yellow crystals, a 52% yield. Elemental analysis are: Obsd.: C, 42.53; H, 6.52; N, 1.01; O (by difference), 49.94. Calculated for $C_{49}H_{84}NO_{40}\cdot 3H_2O$: C, 42.61; H, 6.57; N, 1.01; O, 49.81. The empirical formula, $C_{49}H_{90}NO_{43}$, is very similar to the formula based on 31 units of glucose, 1 unit of fully (two) DAP-substituted sugar ring and three units of water. The degree of substitution in dextran by DAP was 1/32. Other runs varied between 1/28 and 1/45 degree of substitution. Similar results were obtained for aminodextrans prepared from dextrans having nominal average molecular weights of 10K to 2M Da with 1X through 5X-diaminopropane substitution. All the aminodextrans were initially prepared according to the above method using 2 to 5 times the amount of sodium periodate used in the 1X oxidation of dextran. The amount of DAP used for Schiffs' base formation was kept constant. Modifications were made to periodate oxidation, diamine addition, and borohydride reduction reactions. The first modification was to use only a ten percent (10%) excess of diamine over the stoichiometric 2:1 diamine:periodate molar ratio previously used. Second, the diamine addition reaction was conducted at a temperature in the range of 5–10° C. Third, the diamine addition reaction was spectroscopically monitored in the near ultraviolet (UV) region for Schiffs' base formation, which was deemed completed when successive spectral analyses indicated a plateau was reached. The reaction was then stopped. These modifications reduced depolymerization, and thus gave higher yield of product. Elemental analyses for 5X-Amdex, lot -11, which was prepared at a 500 g dextran scale were C=44.45%, H=7.20%, N=3.79%, O (by difference)=44.56%. The empirical formula was $C_{13.7}H_{26.4}O_{10.3}N$, which is similar to the formula $C_{13}H_{24}O_9N\cdot H_2O$ based on 5 units of glucose per one unit of 1.5 diaminopropane-substituted sugar ring ($C_{9.5}H_{21}O_2N_3$), or a degree of substitution of DAP in dextran of ⅙. Similar results were obtained for 5X-Amdex, lot -69 prepared at a 300 g dextran scale.

2. Cross-Linked 5X-Aminodextran.

Crosslinked 5X-Amdex was prepared by a modified procedure. T-2M dextran, 500 g, 3.08 mol, was transferred to a one gallon Waring blendor Model CB6 commercial, stainless steel bowl containing 5000 mL of distilled water. The mixture was blended at ½ maximum speed until all the white solid of dextran was dissolved, typically for about 5 minutes. A solution of 267.5 g, 1.25 mol, of sodium m-periodate in 2000 mL distilled water was added to the dextran solution over a 5–15 minute period using vigorous overhead stirring in a five gallon cylindrical tank. After the periodate addition was completed, the reaction mixture was stirred at room temperature for about an additional four hours. About 5000–6000 mL distilled water were further added to the reaction mixture over the four hour period to reduce the viscosity of the solution. After the four hours, the 12 L reaction volume had an initial specific conductivity of 7.40 mmho-cm$^{-1}$ and an initial pH of 2.65. The reaction mixture was then desalted using a hollow fiber cartridge. Washing was done using about 100 liters of distilled water to obtain 6000 to 9000 mL of washed, oxidized dextran solution having a specific conductance of about 6–20 $\mu$mho-cm$^{-1}$ and pH of 6.5–7.0. Since the dextran aldehyde solution is prone to gelation at ambient temperature, it was first made certain that the dextran aldehyde was completely dissolved before adding DAP. Then, the first portion of DAP, 70 mL of pure liquid, was added over about 5 minutes to the desalted, oxidized dextran solution. The resulting solution immediately began to show formation of a gel, which persisted for another 5–10 minutes before redissolving as a yellow solution. The reaction mixture was then put on an ice bath to maintain a reaction temperature of 8–10° C. and stirred vigorously before a second portion of 70mL DAP was added over a period of 5 minutes. After an additional 10 minutes of stirring, the third and final 70 mL portion of DAP was added to the reaction mixture. The total DAP addition and reaction time was 45 minutes. Then, 70 g, 5.00 mol, of sodium borohydride in 700 mL of 1 mM aqueous potassium hydroxide solution were added to the reaction mixture at 8–10° C. over about 10–15 minutes with overhead stirring. After the sodium borohydride addition was completed, the reaction mixture was stirred for an additional two hours until the yellow Schiffs' base color had disappeared. The reaction mixture was then desalted using the hollow fiber cartridge. In one run at a total volume of 7500 mL, the initial specific conductance was 30.3 mmho-cm$^{-1}$ and the initial pH was 11.79. About 80 L of distilled water were used to produce about 1600 mL of crosslinked 5x-aminodextran solution having a specific conductance of 10–20 $\mu$mho-cm$^{-1}$ and pH of 7.0–8.0. The aminodextran solution was filtered through a 1.6 $\mu$m glass filter and lyophilized for a minimum of 72 hours to produce 75–90 g (15–18% yield) of flaky, white to pale yellow crystals. Analyses for 5X-Amdex, lot 1–5, which gave a good yield of conjugates were C=41.38%, H=7.81%, N=4.15%, O=45.64%, I=97ppm, B=590 ppm. The empirical formula was $C_{11.6}H_{26.1}O_{9.6}N$, which is similar to the formula $C_{11.2}H_{20.3}O_{7.3}N \cdot 2H_2O$ based on 4 units of glucose per one unit of 1.5 diaminopropane-substituted sugar ring. Thus, the degree of substitution of DAP in dextran was ⅕. Similar procedures were used in the preparation of 5X-Amdex, lot 2–2, except ⅓xDAP was added in two portions to give a product which analyzed as C=40.44%, H=7.75%, N=3.48%, O=48.48% with a degree of substitution of DAP of ⅛.

High diamine concentrations caused depolymerization, and thus gave significantly lower molecular weight aminodextrans than the starting dextran. β-elimination and thereby depolymerization [Besemer, A. C., et al, in Cellulose Derivatives: Modification, Characterization, and Nanostructures, T. J. Heinze and W. G. Glasser, Eds. (ACS Symposium Series 688, American Chemical Society, Washington, DC, 1998), Chap.5, pp. 73–82.] has been previously noted in various oxidation reactions of glucans such as cellulose and starch. The periodate oxidation of glucose units in dextran produced by *Leuconostoc mesenteroides* NRRL B-512 was shown [Jeanes, A. and Wilham, C. A, J. Amer. Chem. Soc. 72, 2655 (1950); Van Cleve, J. W., et al., J. Amer. Chem. Soc. 78, 4435 (1956)] to release one mole of formic acid per mole of reacted glucose unit by 95% of the anhydroglucose residues. Thus, the overall redox equation for a two-step periodate oxidation reaction is $2IO_4^- + C_6H_{10}O_5 \rightarrow 2IO_3^- + C_5H_6O_4 + HCOOH + H_2O$, requiring 2 mol periodate per 1 mol glucose unit or 2 mol aldehyde for complete reaction. However, in 5X-Amdex preparations only 1 mol periodate per 2–5 mol glucose units or 2 mol periodate per 5 mol glucose units were used so that the theoretical degree of substitution is ⅕, i.e., 1 glucose unit out of 5 units in dextran is substituted with 2 aldehyde groups. Thus, the maximum degree of substitution of dextran with DAP is also ⅕, i.e., 1 in 5 glucose units in dextran is substituted with 2 DAP groups, assuming no crosslinking of aldehyde groups by DAP.

Some 5X-Amdex lots require further description. In particular, the reaction mixture of the 5X-Amdex, lot 11-6, after addition of DAP and sodium borohydride, was adjusted to pH 8.5 with aqueous hydrochloric acid. It was then desalted, concentrated, and freeze-dried in the previously described manner. Elemental analyses for 5X-Amdex, lot 11-6, were C=39.72%, H=7.77%, N=4.44%, Cl=2.81%, O (by difference)=45.26%. The empirical formula based on actual analyses was $C_{10.4}H_{24.3}O_{8.9}NCl_{0.25}$. The chloride analysis showed that 1 out of 4 total amine (primary and secondary) groups had a chloride counterion. Assuming only primary amine groups would be protonated near neutral pH to which the reaction mixture was desalted prior to lyophilization, this implies that 50% of the diaminopropane groups in aminodextran are bridging or crosslinking groups between dextran chains. These bridging DAP groups contain only two secondary amino groups. Thus, idealized repeating units for solely the substituted glucose residues of aminodextran would contain the following sequences: (a) 1 bridging DAP, 2 non-bridging DAP; 2 bridging DAP; 2 non-bridging DAP, 1 bridging DAP; (b) 2 bridging DAP; 2 bridging DAP; 4 non-bridging DAP; or some permutation of either of the (a) or (b) sequences. A portion of the lyophilized aminodextran hydrochloride was dissolved in distilled water and deionized in batchwise fashion with mixed bed (H$^+$, OH$^-$ form), Bio-Rad AG 501-X8 resin, until the specific conductivity of the supernatant was minimized. The resin was removed by filtration of the suspension through rayon cloth and the aminodextran (~50 mg/mL) in the filtrate was fractionated by precipitation with acetone (0–43% cut). The solid precipitate was washed with acetone and dried in a vacuum dessicator under silica gel. Elemental analyses of this deionized and fractionated material gave C=45.55%, H=7.03%, N=3.82%, Cl<0.5%, O (by difference)=43.60%, showing that chloride ion had been removed.

EXAMPLE 2

Light Scattering, Viscosity, and Refractive Index Data

90° light scattering was measured for dextran and aminodextrans at 10 mg/mL in distilled water in a 1 cm path cell with the COULTER® N4MD sub-micron particle analyzer. Values ranged from $7.4 \times 10^4$ to $1.1 \times 10^5$ counts/sec for dextran, T-2M; from $2.9-3.7 \times 10^4$ counts/sec for 1X-Amdex lots at 10 mg/mL; from $2.5 \times 10^4$ to $1.2 \times 10^5$ counts/sec for 5X-Amdex lots at 10 mg/mL versus distilled water at $4.5 \times 10^3$ counts/sec.

Molecular data for eleven samples, one dextran and ten aminodextrans, determined from duplicate batch analyses by the Viscotek (Houston, Tex.) triple detector system [Haney, M. A., Gillespie, D., and Yau, W. W., Today's Chemist at Work 3(11), 39 (1994)] are summarized in Table 1. The instrumental system consists of a model T-60 differential viscometer/light scattering dual detector and a model LR40 differential laser refractometer with a 670.0 nm diode laser source. The principles of the method and analyses have been described [Haney, cited above]. The samples were run at a concentration of 0.7 to 1.0 mg/mL in 0.2M aqueous sodium nitrate solution through a column consisting of a 50' coil of 0.01" i.d. stainless steel tubing without any column packing in batch mode. Two dissolution protocols were followed: 1. By minimum heating at ~70–80° C. for 5–10 min for samples 1, 3, 5, 6, and 8; 2. By first soaking at room temperature for 1–2 hours and then heating at ~70–80° C. for 30 min for samples 2, 4, 7, 9, 10, and 11. The responses of the three primary detectors are as follows: light scattering. $M \times (dn/dc)^2 \times c$; viscometer, $IV \times c$; refractometer, $dn/dc \times c$. Right angle light scattering gives the molecular weight when combined with viscometry detection. The 90° LS is corrected for angular dissymmetry using the Debye equation, together with the molecular size information provided by the viscometer. Viscometry yields the molecular density, which is related to conformation and branching, and the refractometer measures concentration of sample, providing direct determination of the refractive index increment, $dn/dc$, of the polymer sample. The hydrodynamic volume of a polymer molecule in solution, related to the cube of its radius of gyration, $R_g$, is directly proportional to the intrinsic viscosity (IV or $\eta$) and the weight average molecular weight ($M_w$), divided by Avogadro's number. The accuracy of $R_g$ values determined by the triple detector system is claimed to be within 0.5 nm.

TABLE 1

Triple Detector System Data for Dextran and Various Aminodextrans.

| Sample | Conc., mg/mL | dn/dc, mL/g | $M_w$, kDa | IV, dL/g | $R_g$, nm | R, nm |
|---|---|---|---|---|---|---|
| 1. 5X-Amdex, lot-11 | 0.860 | 0.155 | 414 | 0.262 | 15.6 | 38.2 |
| 2. 5X-Amdex, lot-11 | 1.940 | 0.132 | 25.6 | 0.0602 | 3.79 | 9.28 |
| 3. 1X-Amdex | 0.940 | 0.155 | 1,044 | 0.442 | 25.2 | 61.7 |
| 4. 1X-Amdex | 3.480 | 0.132 | 93.9 | 0.205 | 8.80 | 21.5 |
| 5. Dextran, T-2M | 0.800 | 0.147 | 2,102 | 0.609 | 35.5 | 87.0 |
| 6. 5X-Amdex, lot 1-5 | 0.800 | 0.190 | 70.0 | 0.167 | 7.38 | 18.1 |
| 7. 5X-Amdex, lot 1-5 | 3.010 | 0.132 | 34.4 | 0.100 | 4.96 | 12.1 |
| 8. Amdex-3M | 0.770 | 0.155 | 2,999 | 0.674 | 41.3 | 101.2 |
| 9. 5X-Amdex, lot-69 | 2.400 | 0.132 | 69.95 | 0.141 | 7.06 | 17.3 |
| 10. 5X-Amdex, lot 11-6 | 2.610 | 0.132 | 44.5 | 0.0999 | 5.40 | 13.2 |
| 11. 5X-Amdex, lot 2-2 | 2.390 | 0.132 | 168.4 | 0.186 | 10.35 | 25.3 |
| Dextran* | | | 54,600 | | 70.0 | |
| Dextran** | | | 65 | | | 25.0 |
| Dextran** | | | 20 | | | 20.0 |
| Dextran** | | | 500 | | | 45.0 |

*Bovey, F. A., J. Polym. Sci. 35, 167(1959).
**Titova, E. F., et al, Farmatsiya 23(5), 12(1974).

Data for eleven samples were used to construct a Mark-Houwink plot of log (IV) versus log ($M_w$) as shown in FIG. 1. Linear regression analysis for all data gave a correlation coefficient of 0.976, a Y-intercept of −3.062, and a slope of 0.451. The slope corresponds to the exponent in the Mark-Houwink-Sakurada equation, $[\eta]=KM^a$, and in the above samples the value is very similar to the $a=0.50$ one obtained for the linear fraction of dextran of 20,000 to 100,000 Da in water at 25° C. as compiled [Kurata, M. and Tsunashima, Y., Polymer Handbook, J. Brandrup and E. H. Immergut, Eds. (Wiley-Interscience, New York, 1989) Chap. VII, pp. 1–55.]. This value of the exponent, $a=0.50$, has been established for linear, flexible polymers under 'theta' temperature or solvent conditions, whereas the branched fraction of dextran of 800,000 Da in water at 25° C. gave $a=0.20$. It was therefore concluded that the aminodextrans behave as flexible, linear chains arranged in a compact, globular structure in aqueous sodium nitrate solution and the positive charges of primary amino groups in 5X-Amdex are not sufficient to affect the compact dextran structure. The radius of gyration for a randomly coiled, linear, polymer molecule has been derived from random walk statistics as $R_g^2 = \frac{1}{6}nl^2$, where n is the number of statistical segments in the polymer chain and l is the length of each statistical segment. Also, the mean square end-to-end distance in a random coil is given by $R^2=nl^2$ [Hiemenz, P. C., Principles of Colloid and Surface Chemistry (Marcel Dekker, New York, ed. 2, 1986) pp. 102–107]. Thus, it becomes possible to use the accurate $R_g$ and mass average molecular weight values obtained from light scattering and viscosity, and elemental analyses (empirical formulae and degree of substitution) to calculate the root mean square end-to-end distance, R, the average molecular mass per segment, $M_i$, the number of statistical segments, and a statistical segment length in each polymer. These latter values can then be compared to the length of a single unit of 1,6-linked glucose reported [Bovey, F. A., J. Polym. Sci 35, 167 (1959)] as about 8 Å long. Statistical segment lengths were 7.5 to 9.0 Å for the aminodextrans. Free rotation about the methylene group between residues of 1,6-glucosyl units in dextran appears to confer extra flexibility on the dextran chain in contrast to the rigidity of the chain of 1,4-glucosyl units in cellulose nitrate [Doty, P., et al., J. Amer. Chem. Soc. 75, 754 (1953)] in which glucose residues are joined only by an ether linkage. Previous studies of dextran of molecular weight greater than 2,000 Da have all indicated a globular structure [Bovey, cited above; Titova, cited above] in contrast to the open, extended structures of fiber and extracellular matrix polysaccharides such as cellulose and proteoglycans.

EXAMPLE 3

Gel Electrophoresis of Aminodextrans

Figure 2:
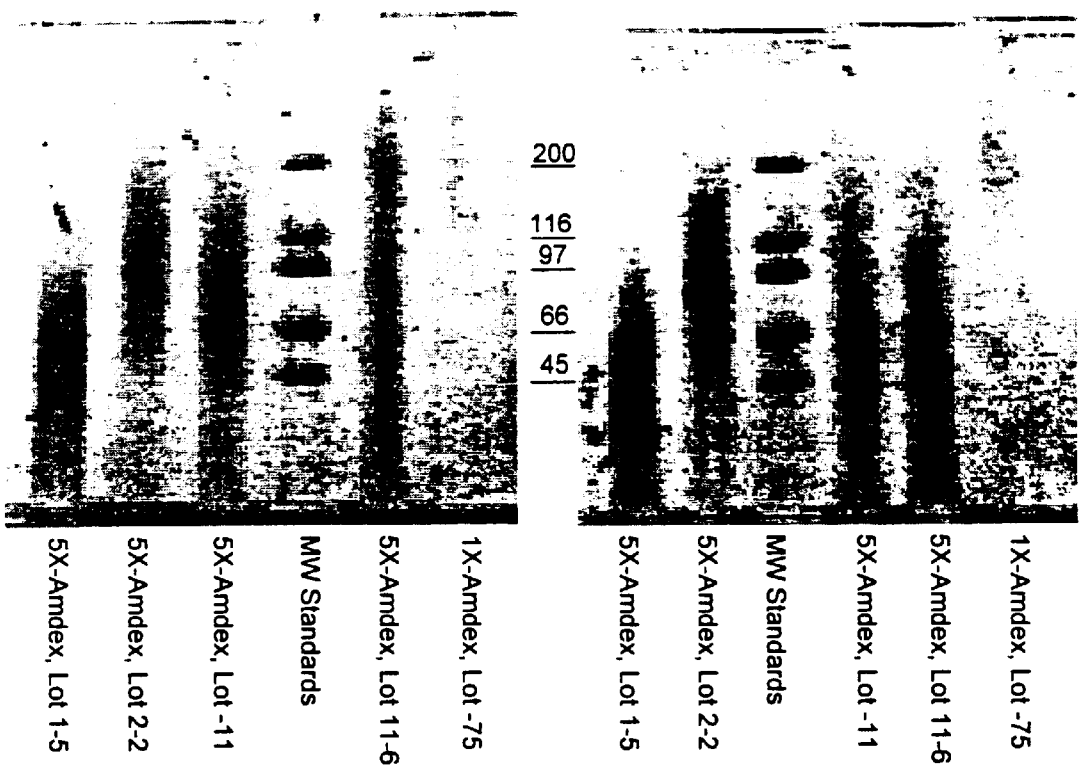
FIG. 2 shows the SDS-PAGE results for various amino-dextran lots dissolved in 1×PBS buffer solution: LHS, protocol 1 dissolution; RHS, protocol 2 dissolution. In each set, lanes 1 to 6 from L to R contain 5X-Amdex, lot 1-5; 5X-Amdex, lot 2-2; 5X-Amdex, lot -11; 5X-Amdex, lot 11-6; and 1X-Amdex, lot -75, respectively. The lane containing five narrow bands contains the molecular weight standards.

Phosphate-buffered saline, 1×PBS, pH 7.1–7.3, and conductivity 13,500–15,500 $\mu$mho-cm$^{-1}$, was prepared by dilution with distilled water from a 20×PBS stock solution, which contains 26.9 g dm$^{-3}$ of $K_2HPO_4$, 6.4 g dm$^{-3}$ of $KH_2PO_4$, and 170.0 g dm$^{-3}$ of NaCl. Sodium dodecyl sulfate-polyacrylamide gel electrophoresis (SDS-PAGE) of aminodextrans were run at 400V (65V-h) on the Pharmacia PHAST system, using a 4–15 gel gradient for the 30 to 300 kDa molecular weight range and SDS buffer strips. The use of this system for aminodextrans is made possible by the protonation and, thus, charging of primary amine groups at pH 8.0 of SDS buffer strips and the selective electrostatic interaction between negatively-charged sulfonate groups of the widely-used Coomassie blue stain (Pierce Catalog) and protonated amine groups. Since electrophoresis, applied to the study of synthetic polyelectrolytes, has been shown [Smisek, D. L. et al., Macromolecules 22, 2270 (1989)] to provide a more detailed molecular weight distribution than size exclusion chromatography, we had hoped to obtain an accurate measure of the size distribution in aminodextrans from the spread of bands in the electrophoretograms. Some lots of solid aminodextran resisted dissolution in aqueous media; thus, two protocols were needed to test samples for complete dissolution. In protocol 1, minimum heating of samples in distilled water at ~70–80° C. was carried out for 5–10 min whereas, in protocol 2, the samples were similarly heated for 30 min. Both dissolution protocols were used to prepare 1 mg/mL Amdex solutions in 1×PBS buffer, each mixed 1:1 with SDS buffer, which were then run together with a high molecular weight (200, 116, 97, 66, and 45 kDa) standards sample. Gel electrophoresis bands stained with Coomassie blue for the two runs are shown in FIG. 2. Molecular weight ranges were estimated for the aminodextrans from the range of the heaviest blue stain in each lane of the gel, referenced to the relatively narrow band positions of five standards in the same gel. 5X-Amdex lots 1-5, 2-2, -11 and 11 -6, and 1X-Amdex lot -75 gave molecular weight ranges of about 30–75, 60–190, 50–150, 35–250, and 150–250 kDa, respectively, for protocol 1 dissolution and about 30–75, 55–175, 40–90, 30–110, and 150–250 kDa, respectively, for protocol 2 dissolution. The 5X-Amdex lots showed the largest change to lower molecular weight fragments with the more extensive protocol 2 dissolution procedure. In most cases, the average molecular weight determined from the Viscotek triple detector (light scatter, viscosity, refractive index) system measurements fell in the middle of the range shown by SDS-PAGE results, even though the position of species in electrophoretograms depends strictly on their charge-to-size ratio.

EXAMPLE 4

Preparation of CdS Nanoparticles of the Invention

All solutions related to the preparation of CdS nanoparticles were freshly prepared and were filtered through 0.22 Am pore size membranes before each experiment. The UV-visible spectra of CdS dispersions were recorded with a Perkin Elmer Lambda 6 UV/vis or Beckman DU640 spectrophotometer. The size of CdS nanoparticles was determined from the onset of light absorption based on the previously published calibration curve [Weller, H., et al., Chem. Phys. Lett. 124, 557 (1986)]. The luminescence emission spectra of Amdex-CdS dispersions were recorded with the Spex Fluorolog instrument equipped with a Tracor Northern TN 6500 rapid scan spectrometer detection system, using 380 nm excitation.

A. Controlled Double-Jet Precipitation Process

The equipment for the controlled double-jet precipitation (CDJP) was described in detail previously [Wang, L., et al., Colloid Polym. Sci. 275, 593 (1997); Schultz, M., and Matijevic, E., Colloids Surf. 131, 173 (1998); Lee, S. -H. et al., J. Colloid Interface Sci. 186, 193 (1997)]. In a typical run, equal volumes (50 cm$^3$) of solutions containing the Cd(II) salt and $Na_2S$, respectively, were simultaneously introduced by peristaltic pumps into the jacketed reactor at a constant flow rate of 10 cm$^3$ min$^{-1}$. The reactor contained 100 cm$^3$ of an aqueous 5x-aminodextran solution, stirred at 700 rpm. The reactor outer jacket was connected to a thermostated circulating water bath kept at 25.0±0.1° C. The mixing of the solutions immediately yielded CdS sols, which were further stirred for 15 min. The summary of experimental conditions used in these experiments is given in Table 2, below.

To establish the dependence of the particle size and of the optical properties of the resulting CdS dispersions on the type of the anion present in Cd(II) salts, equal volumes of $1 \times 10^{-3}$ M solutions of $CdCl_2$, $Cd(NO_3)_2$, $CdSO_4$, and $Cd(ClO_4)_2$, respectively, were reacted with a $1 \times 10^{-3}$ M $Na_2S$ solution. The final concentration of CdS and of 5x-aminodextran was $2.5 \times 10^{-4}$ M and 2.5 g dm$^{-3}$ respectively. To establish the effect of the reactant concentrations, the experiments were also carried out using higher (up to $1 \times 10^{-1}$ M) concentrations of $CdSO_4$ and $Na_2S$.

To enhance the luminescence intensity of the synthesized CdS dispersions, in some experiments a higher concentration of Cd(II) salts ($1.3 \times 10^{-3}$ M) was used, while the concentration of $Na_2S$ was kept the same, still maintaining the same volumes of the reactant solutions. For this reason, a few drops of 0.1 M NaOH solution were also added to the prepared CdS dispersions to reach pH ~11.

B. Rapid Mixing of Reactant Solutions

This procedure consisted of rapidly adding 100 cm$^3$ of a $CdSO_4$ solution into 100 cm$^3$ of a stirred $Na_2S$ solution containing 5 g dm$^{-3}$ of 5x-aminodextran, keeping $[Cd^{2+}]/[S^{2-}]=1$. The concentrations of the $CdSO_4$ and $Na_2S$ solutions used in these experiments are given in Table 2.

TABLE 2

Conditions for the preparation of nanosized CdS particles by the CDJP and rapid mixing processes. The final concentration of 5x-aminodextran, lot 11-6 is 2.5 g dm$^{-3}$.

| Sample | Initial concentrations of $CdSO_4$ + $Na_2S$ solns (M) | pH | Final CdS concentration (M) | Estimated Particle Size (nm) | Suspension Stability |
|---|---|---|---|---|---|
| | | CDJP process | | | |
| a | 0.001 | 9.1 | 0.00025 | 2.7 | stable |
| b | 0.01 | 9.0 | 0.0025 | 4.0 | stable |
| c | 0.1 | 8.8 | 0.025 | ~8.0 | stable |
| | | Rapid mixing process | | | |
| a1 | 0.0005 | 9.1 | 0.00025 | 2.2 | stable |
| b1 | 0.005 | 9.0 | 0.0025 | 3.1 | stable |
| c1 | 0.05 | 8.8 | 0.025 | — | unstable |

In order to evaluate the effects of different aminodextrans (5x-aminodextran, lots 11-6, 1-5, and 2-2, 1x-aminodextran, Amdex-3M, and Amdex-3000) on the size, stability, and fluorescence, CdS nanoparticles were prepared by the rapid mixing 50 cm$^3$ of a $1.5 \times 10^{-3}$ M $Cd(ClO_4)_2$ solution with 50 cm³ of a solution containing $1\times10^{-3}$ M $Na_2S$ and varying concentrations of aminodextrans between 0.05 and 16 g dm⁻³. The same experiments were carried out with dextran 500,000, in concentrations of 2, 5, and 20 g dm⁻³, and with 5 g dm⁻³ of dextran 20,000. The mixing of the solutions immediately yielded CdS sols, which were further stirred for 15 minutes. In all samples the pH was raised with NaOH to ~10.5.

C. Size of Nanoparticles Prepared by (A) CDJP and (B) Rapid Mixing

Figure 3:
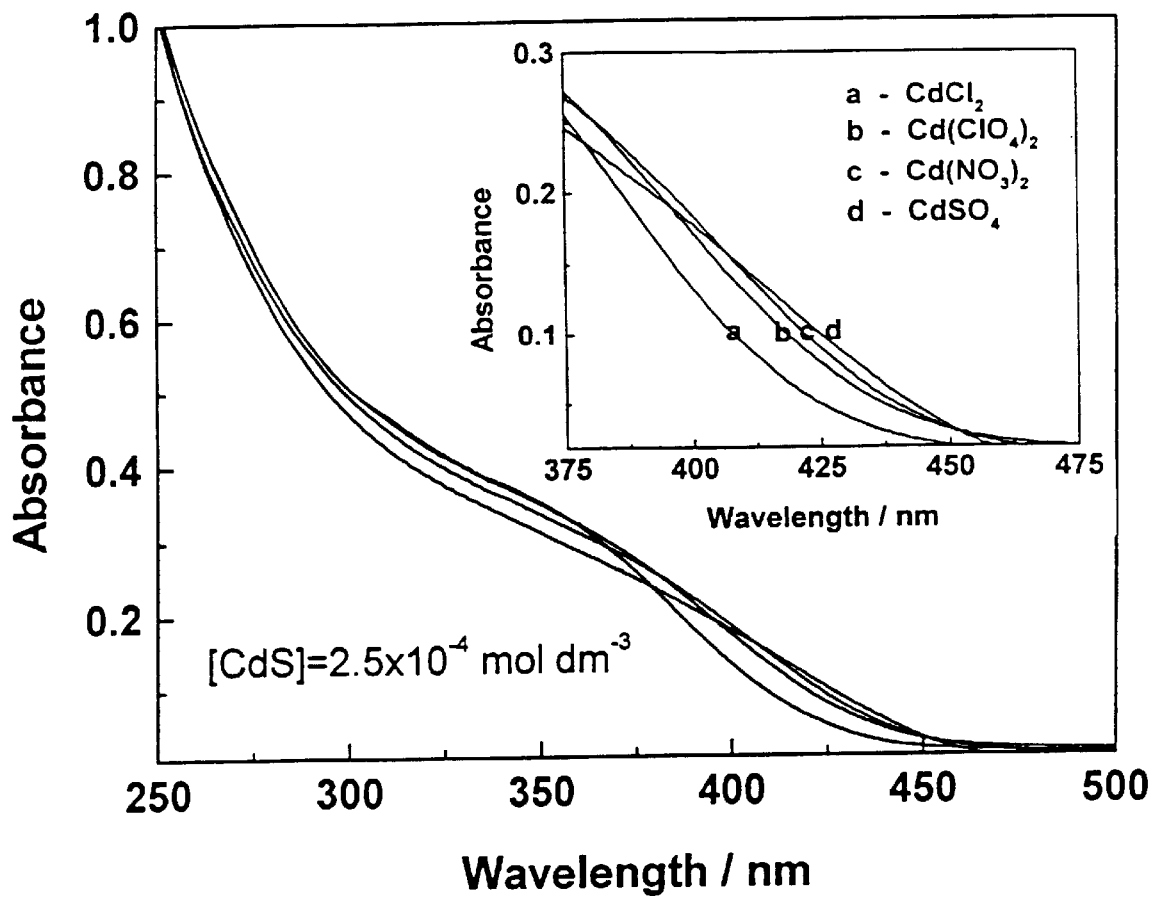
FIG. 3 provides the absorption spectra of CdS nanoparticles prepared by the controlled double-jet precipitation (CDJP) process using $1\times10^{-3}$ mol dm$^{-3}$(M) Na$_2$S, $1\times10^{-3}$ mol dm$^{-3}$(M) (a) CdCl$_2$, (b) Cd(ClO$_4$)$_2$, (c) Cd(NO$_3$)$_2$, (d) CdSO$_4$ solutions, and 5 g dm$^{-3}$ of 5x-aminodextran, lot 11-6.

The absorption spectra of CdS dispersions prepared with different Cd(II) salts and 5x-aminodextran, lot 11-6 as stabilizer (FIG. 3) and diluted to $[CdS]=2.5\times10^4$ M were used to evaluate the size of the resulting nanoparticles. Thus, the sols obtained with the $CdCl_2$ solution show the absorption onset of $\lambda_o$~425 nm (spectrum a), corresponding to the average particle size of 2.3 nm, while those precipitated with $Cd(NO_3)_2$, $CdSO_4$, and $Cd(ClO_4)_2$ solutions had a diameter of 2.7 nm ($\lambda_o$~455 nm, spectra b, c, and d).

Figure 4:
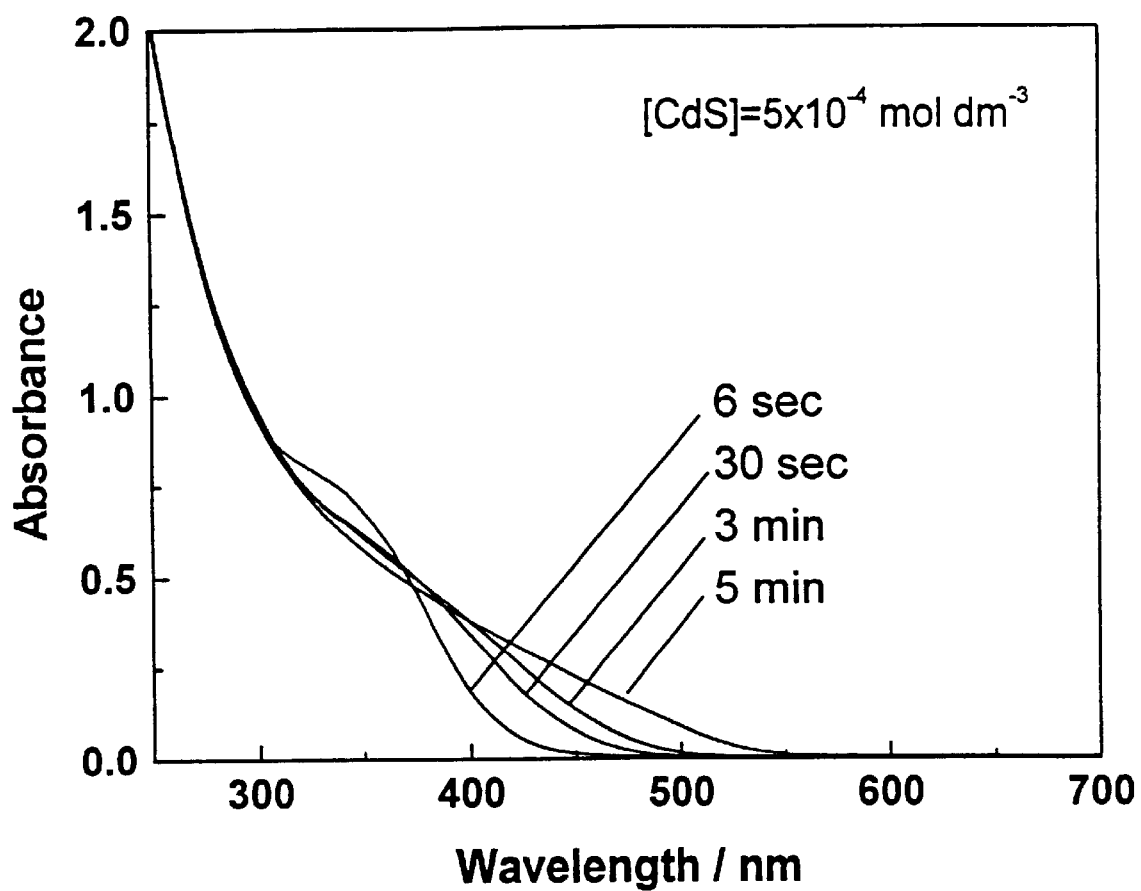
FIG. 4 provides the absorption spectra of CdS samples collected after 6 s, 30 s, 3 min, and 5 min after the beginning of the CDJP process. The concentrations of CdSO$_4$ and Na$_2$S solutions were $1\times10^{-3}$ mol dm$^{-3}$(M), and of 5x-aminodextran, lot 11-6, 5 g dm$^{-3}$.

FIG. 4 displays the change in the absorption spectrum of the CdS dispersion with time during the CDJP process, after dilution to $[CdS]=5\times10^{-4}$ M. The shift in the absorption onset towards higher wavelengths indicates an increase of the particle size from 2.3 nm after 6 seconds to approximately 8 nm after 5 min.

Figure 5:
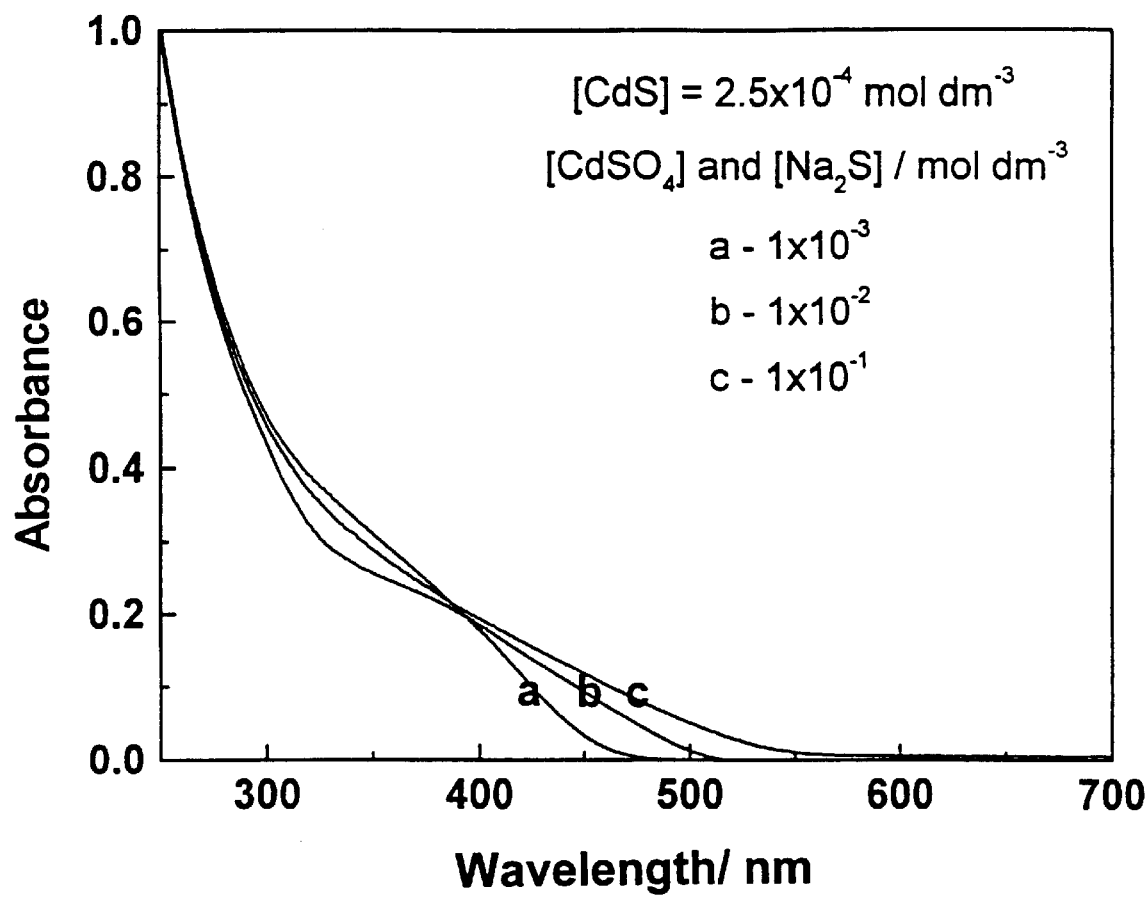
FIG. 5 provides the absorption spectra of CdS nanoparticles prepared by the CDJP using (a) $1\times10^{-3}$, (b) $1\times10^{-2}$, and (c) $1\times10^{-1}$ mol dm$^{-3}$(M) CdSO$_4$ and Na$_2$S solutions using 5 g dm$^{-3}$ of 5x-aminodextran, lot 11-6 as stabilizer.
Figure 6:
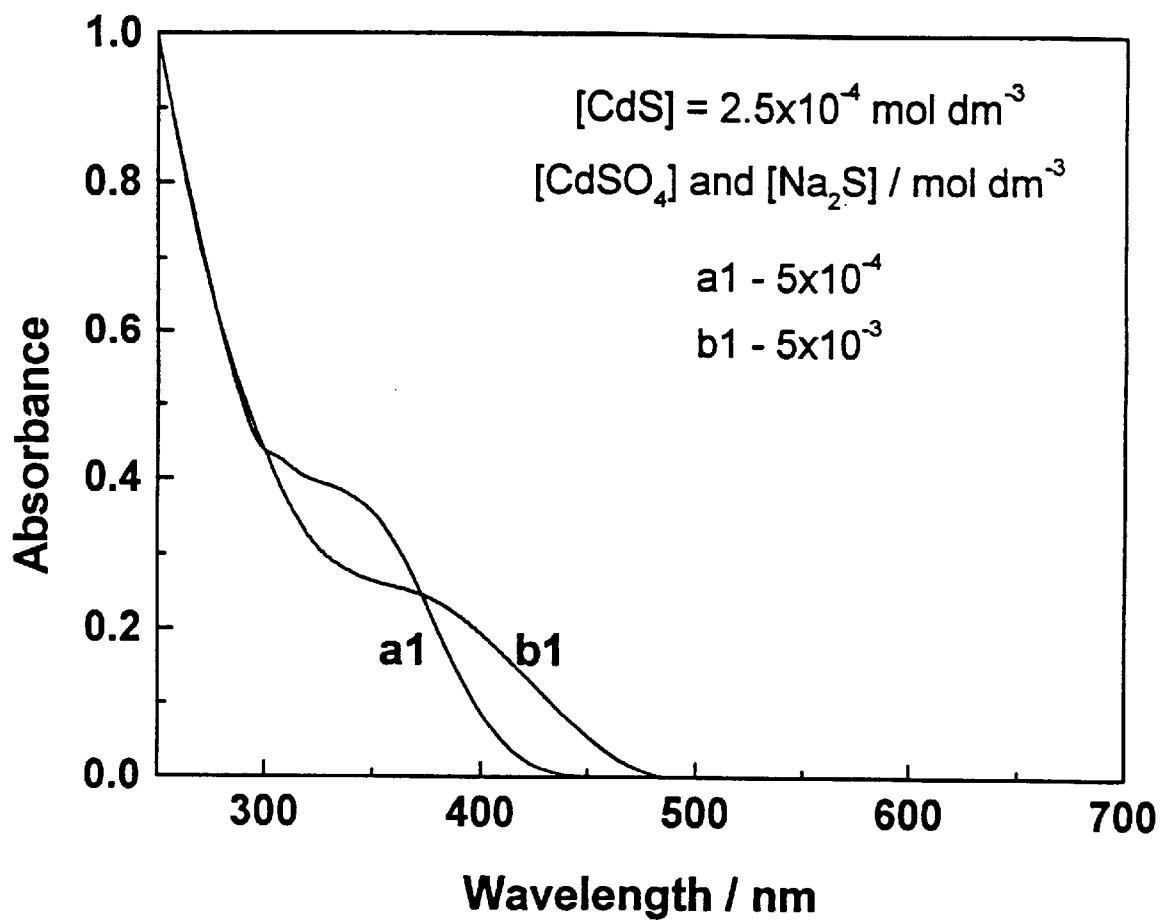
FIG. 6 provides the absorption spectra of CdS nanoparticles prepared by the rapid mixing of (a1) $5\times10^{-4}$ and (b1) $5\times10^{-3}$ mol dm$^{-3}$(M) CdSO$_4$ and Na$_2$S solutions using 5 g dm$^{-3}$ of 5x-aminodextran, lot 11-6 as stabilizer.

The effect of different concentrations of $CdSO_4$ and $Na_2S$ solutions on the particle size of the resulting CdS dispersions containing 5x-aminodextran, lot 11-6 is shown in FIG. 5. For comparison purposes all dispersions were diluted to the same concentration of $[CdS]=2.5\times10^{-4}$ M. The onset of absorption rose from 460 nm to 540 nm, as the reactant concentrations were increased from $1\times10^{-3}$ to $1\times10^{-1}$ M. The former onset value corresponds to particles of 2.7 nm, while the latter is indicative of the formation of larger particles, whose size can not be established from the calibration curve given in Weller, H., et al., Chem. Phys. Lett. 124, 557 (1986). It may, however, be estimated from the results reported in Weller, H., Angew. Chem. Int. Ed. Engl. 32, 41 (1993), that the size of these particles is approximately 8 nm. Analogous trend was observed with CdS nanoparticles prepared by the rapid mixing process (FIG. 6), i.e., the particle size shifted from 2.2 to 3.1 nm when the molar concentrations of $CdSO_4$ and $Na_2S$ were changed from $5\times10^{-4}$ to $5\times10^{-3}$ M.

The results obtained with the two procedures suggest that, under the same conditions, the CDJP and rapid mixing techniques yielded dispersions containing CdS nanoparticle. However, the rapid mixing yielded consistently smaller CdS particles than the CDJP (Table 2). Furthermore, dispersions obtained at higher reactant concentrations were more stable when the CDJP process was employed.

These differences in suspension stability and particle size at otherwise identical final concentrations of CdS suggest, that the mechanism of particle formation by the two processes differs. During the CDJP the reactants are simultaneously fed into the reactor, allowing for a continuous formation of nuclei, which then may aggregate into larger clusters. The particle growth is confirmed by the gradual increase in the absorption onset values during the precipitation process (FIG. 4). These results agree with the observed changes in the suspension color: from pale yellow at the beginning of the precipitation process, to light orange at the end of it. The rapid mixing process results in an instantaneous larger nuclei concentration because of the higher supersaturation. These nuclei then grow to smaller particles (Table 2), probably by the diffusion mechanism. The lower stability of these dispersions is probably due to the larger specific surface area of smaller particles, which means that larger amounts of the polymer are required to stabilize the system.

Figure 7:
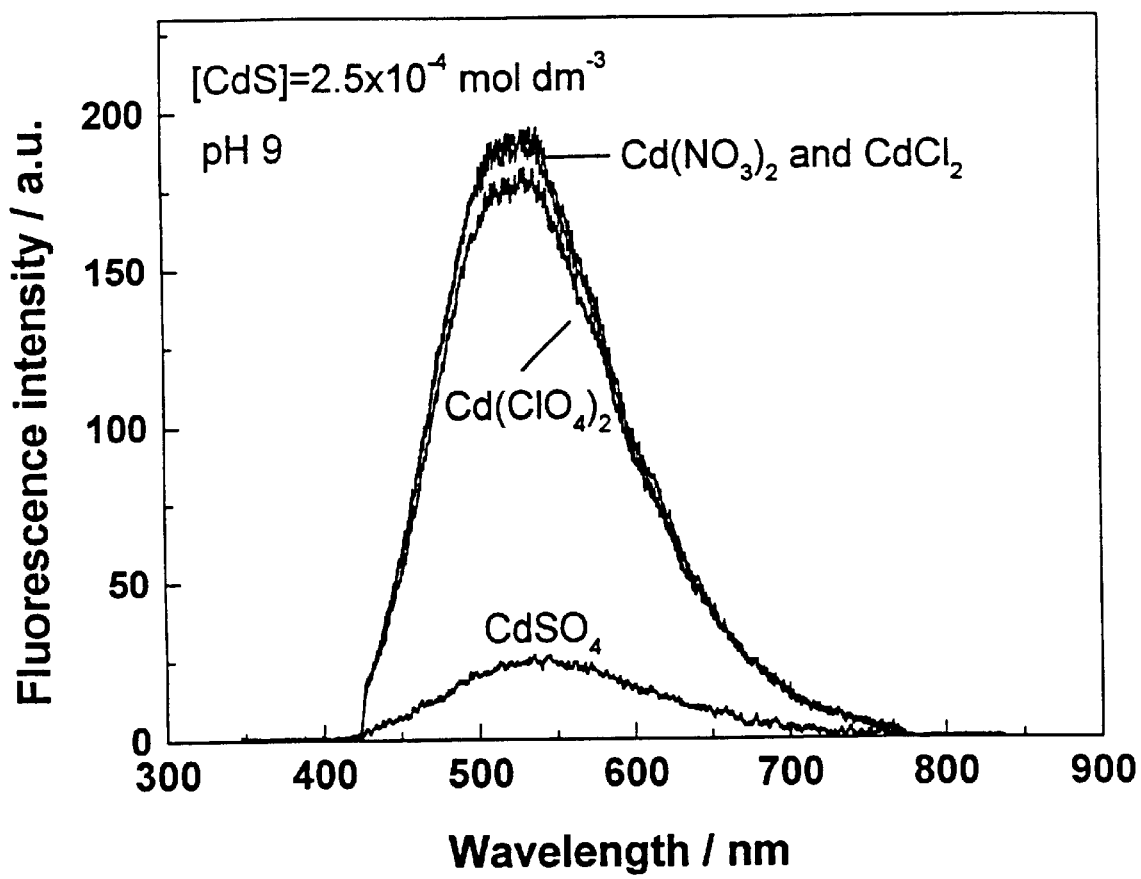
FIG. 7 provides the luminescence emission spectra of CdS nanoparticles prepared by the CDJP using $1.3\times10^{-3}$ mol dm$^{-3}$(M) of CdCl$_2$, Cd(ClO$_4$)$_2$, Cd(NO$_3$)$_2$, and CdSO$_4$ solutions and $1\times10^{-3}$ mol dm$^{-3}$(M) of Na$_2$S solution. The final concentrations of CdS and 5x-aminodextran, lot 11-6 were $2.5\times10^{-4}$ mol dm$^{-3}$(M) and 2.5 g dm$^{-3}$, respectively.

The luminescence spectra of CdS suspensions, prepared by the CDJP process, show that at equal final concentrations of CdS at pH approximately 9 the emission intensity of particles obtained with $CdSO_4$ is much lower than that of systems made with other Cd(II) salts (FIG. 7). In all cases the luminescence intensity maximum is at ~540 nm with the band gap edge at 500 nm and the trap luminescence at longer wavelengths. Thus, the type of anions supplied with cadmium salts has a strong effect on both the size and the emission intensity of CdS nanoparticles, as demonstrated in FIGS. 3 and 7. The effects of anions on the luminescence quenching has been described previously [Henglein, A., Ber. Bunsenges. Phys. Chem. 86, 301 (1982)], who assumed that the positive holes on the semiconductor surface, prior to their recombination with electrons, form ion-pair-type surface complexes with the anions, which quench the luminescence. Among the anions tested, the $SO_4^{2-}$ ions probably have the strongest affinity towards the CdS surface, thus making the emission least intense.

Figure 8:
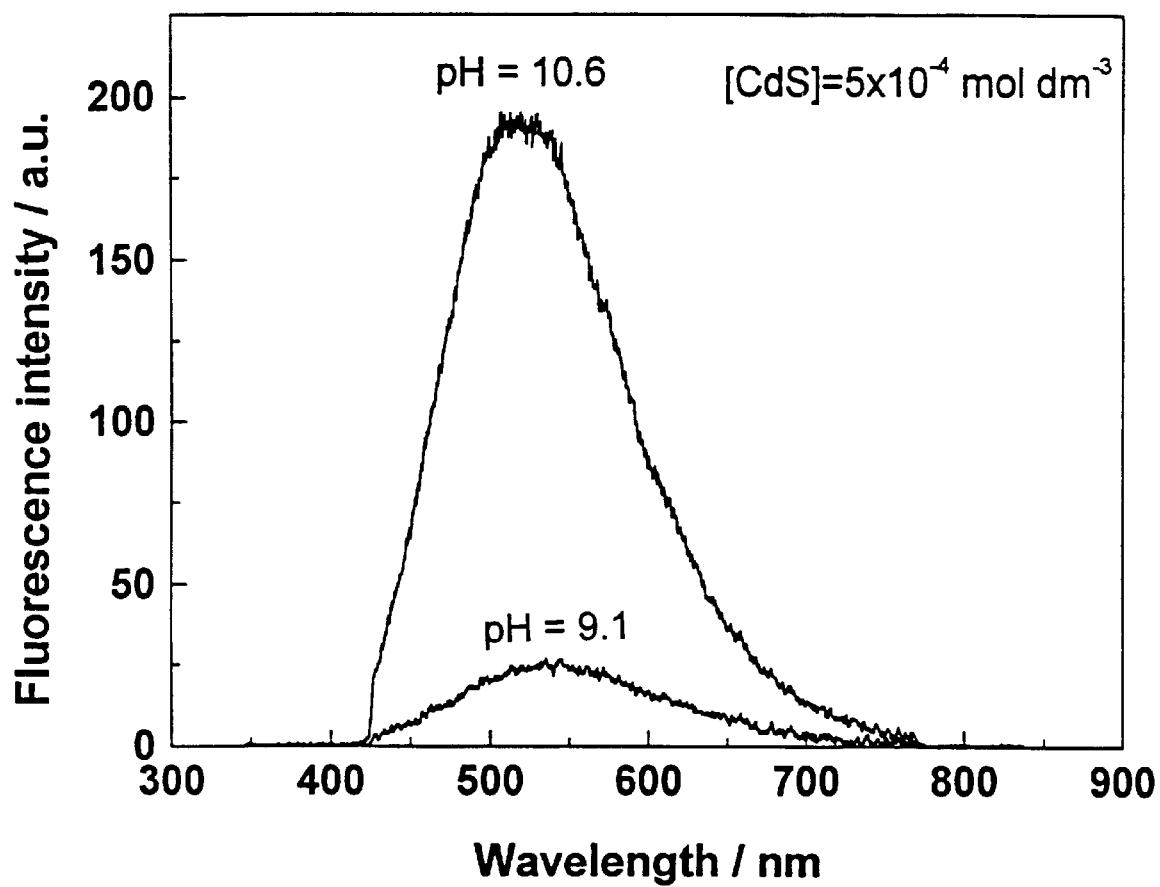
FIG. 8 illustrates the effect of the pH on the intensity of the luminescence emission of CdS dispersion prepared with CdSO$_4$ and Na$_2$S solutions under the same conditions as in FIG. 7.

The activation of luminescence by increasing the system pH in the 30% molar excess of $Cd^{2+}$ is clearly demonstrated in FIG. 8. The emission intensity of the same CdS suspension is significantly higher at pH 11 than at pH 9. This significant increase in the emission intensity of CdS dispersions at higher pH values (FIG. 8) may be caused by the formation of a $Cd(OH)_2$ layer on the CdS surface, which blocks surface imperfections responsible for the trapping of charge carriers. The $Cd(OH)_2$ layer also increases the rate of radiative recombination at the expense of the non-radiative one [Weller, H., Angew. Chem. Int. Ed. Eng. 32, 41 (1993); Spanhel, L., J. Am. Chem. Soc., 109 5649 (1987)].

Figure 9:
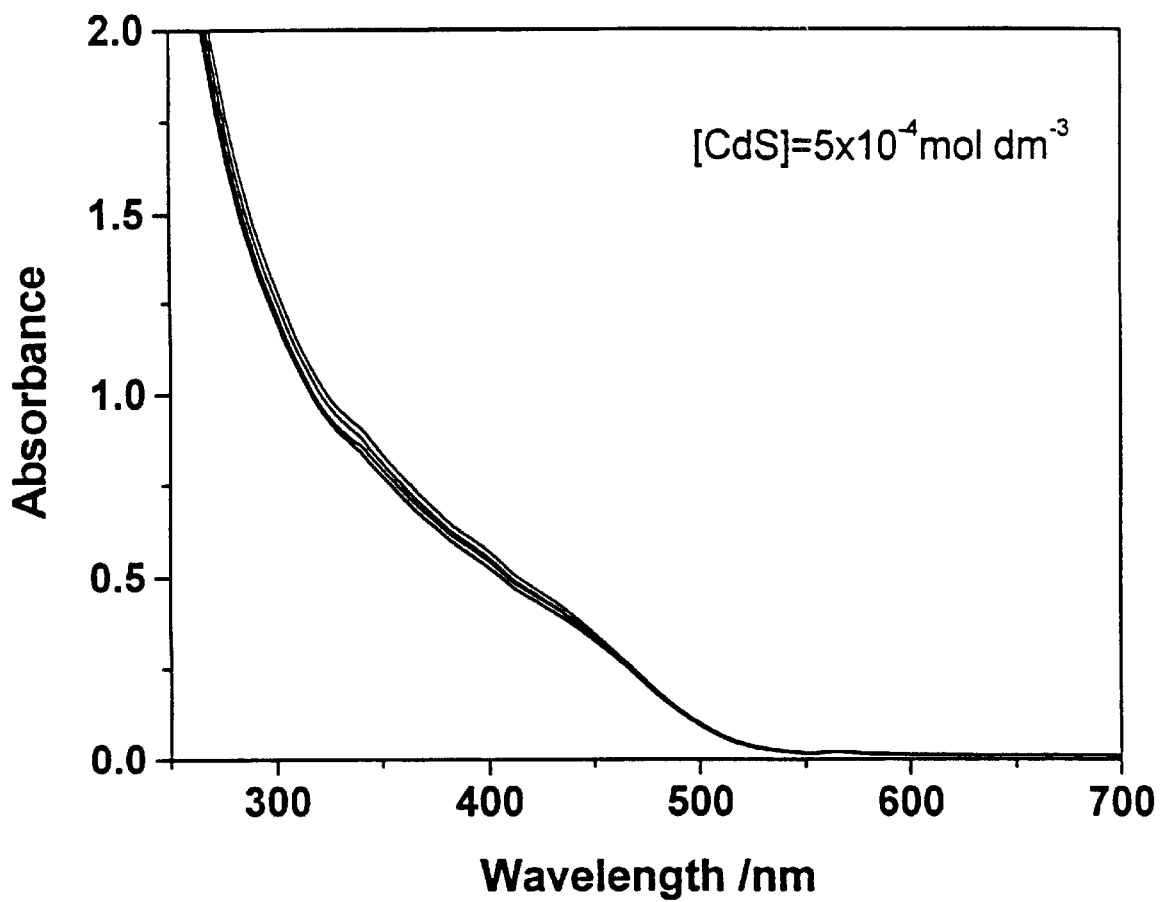
FIG. 9 provides the absorption spectra of CdS nanoparticles prepared with $3\times10^{-3}$ mol dm$^{-3}$(M) Cd(ClO$_4$)$_2$ and $2\times10^{-3}$ mol dm$^{-3}$(M) Na$_2$S solutions using different concentrations of dextran 500,000 (2, 5, and 20 g dm$^{-3}$), and 5 g dm$^{-3}$ of dextran 20,000.

D. The Effect of Different Dextrans and Aminodextrans on the Size, Stability, and Luminescence of CdS Nanoparticles The absorption spectra (FIG. 9) of CdS nanoparticles show the absorption onset of 515 nm for all concentrations of dextran 500,000 used in the preparation. The same absorption onset was also obtained with a CdS dispersion containing 5 g dm⁻³ of dextran 20,000. The particle diameter is estimated to be >5 nm [Henglein, A. Chem Rev. 89, 1861 (1989); Fojtik, A., et al, Ber. Bunsenges. Phys. Chem., 88, 969 (1984)]. None of these suspensions were luminescent.

Figure 10:
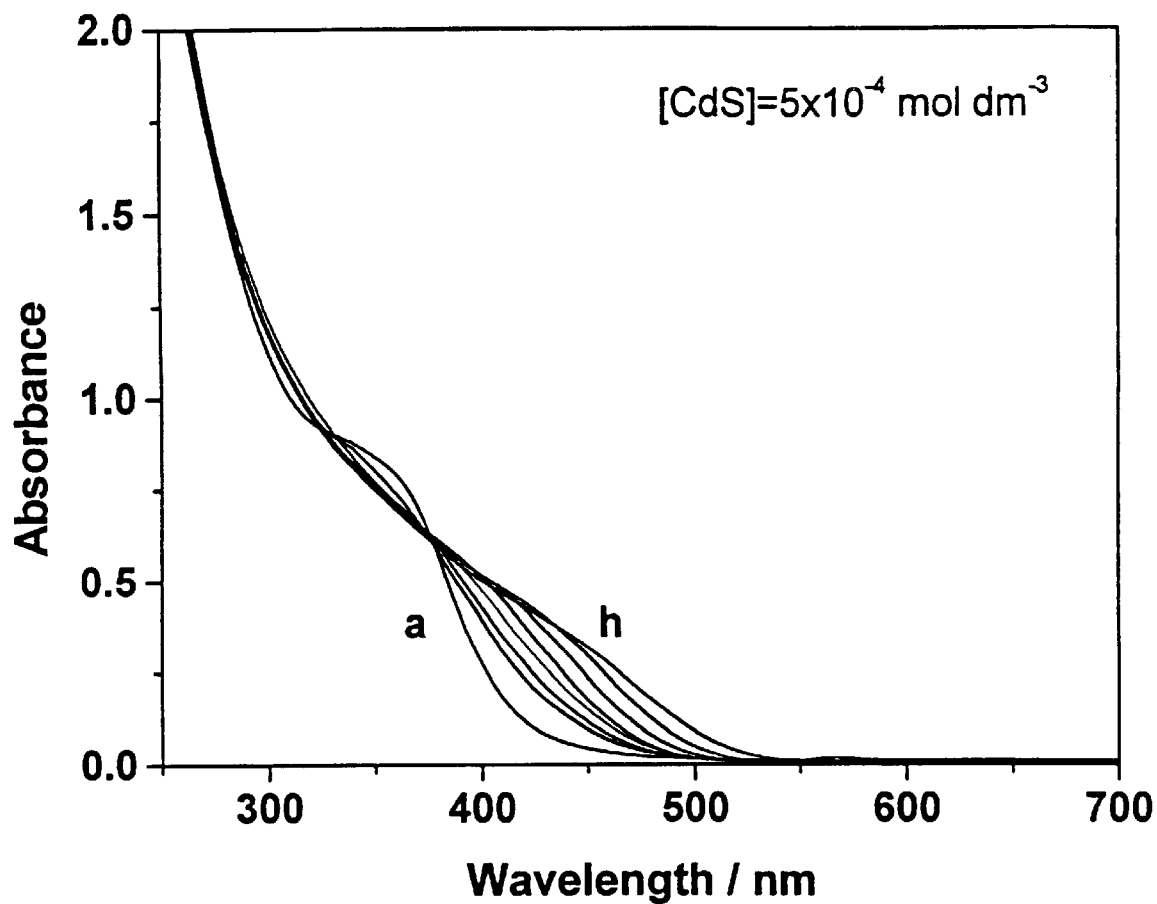
FIG. 10 provides the absorption spectra of CdS nanoparticles prepared with $3\times10^{-3}$ mol dm$^{-3}$(M) Cd(ClO$_4$)$_2$ and $2\times10^{-3}$ mol dm$^{-3}$(M) Na$_2$S solutions using different concentrations of 1x-aminodextran as a stabilizer: 16 (a), 8 (b), 4 (c), 2 (d), 1 (e), 0.5 (f), 0.2 (g), and 0.05 (h) g dm$^{-3}$.

The use of amine-derivatized polysaccharides, aminodextrans, has a significant effect on the size and absorption properties of CdS nanoparticles; i.e., in the presence of high polymer concentrations, the absorption spectra are well structured and steep absorption onsets are in the blue wavelength range (FIG. 10) indicating a narrow size distribution of the dispersions. Specifically, increasing the concentrations of 1x-aminodextran from 0.05 to 16 g dm⁻³, while keeping the same concentrations of other reactants, resulted in shift of the onset of the absorption from 520 nm (spectrum h, particle size>5 nm) to 420 nm (spectrum a, particle size=2.3 nm) (FIG. 10). The CdS dispersions prepared with this polymer in concentrations>1 g dm⁻³ remained stable for about one month, while those with smaller amounts were stable only for a few days.

Figure 11:
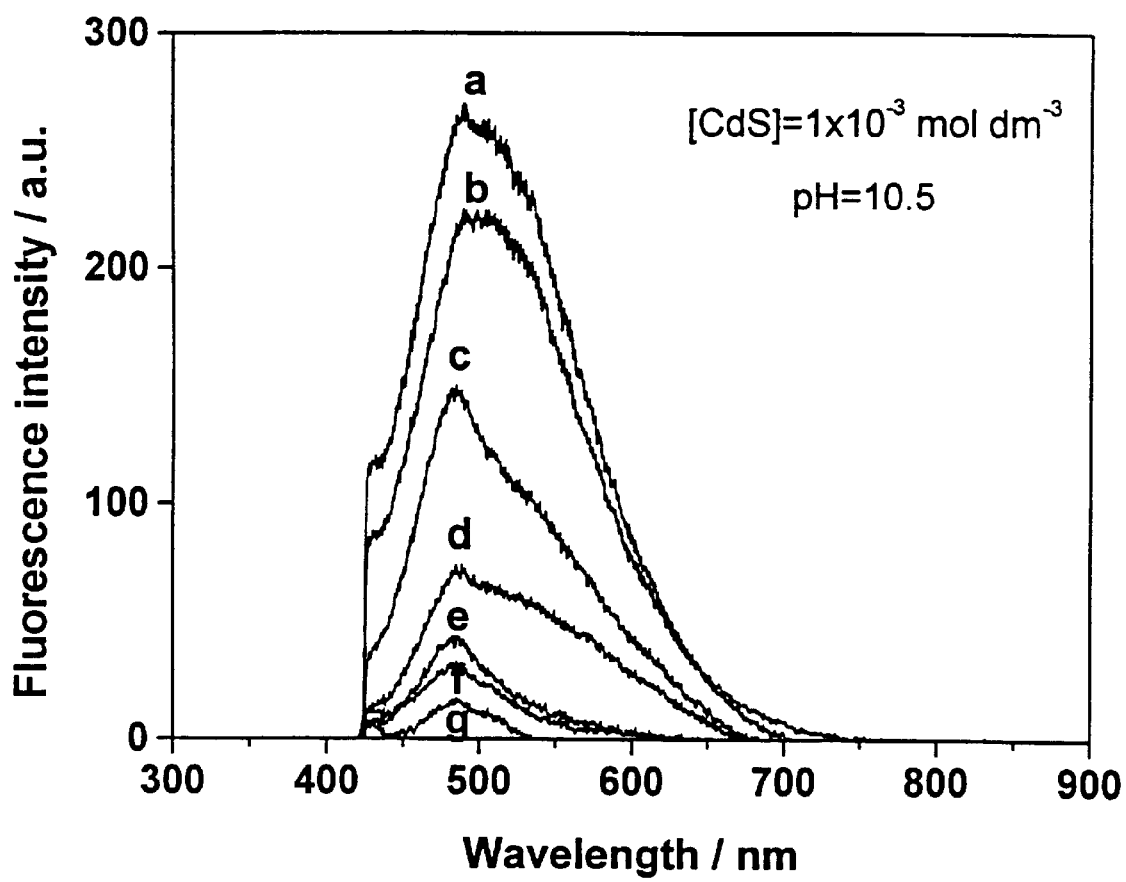
FIG. 11 provides luminescence spectra of CdS nanoparticles prepared with $3\times10^{-3}$ mol dm$^{-3}$(M) Cd(ClO$_4$)$_2$ and $2\times10^{-3}$ mol dm$^{-3}$(M) Na$_2$S solutions using different concentrations of 1x-aminodextran as a stabilizer: 16 (a), 8 (b), 4 (c), 2 (d), 1 (e), 0.5 (f), and 0.2 (g) g dm$^{-3}$.

FIG. 11 shows that the relative luminescence intensity is higher with increasing concentration of 1x-aminodextran, with a maximum at 490 nm, shifting to 500 nm at the largest Amdex concentration, and a bandwidth of about 150 nm.

Figure 12:
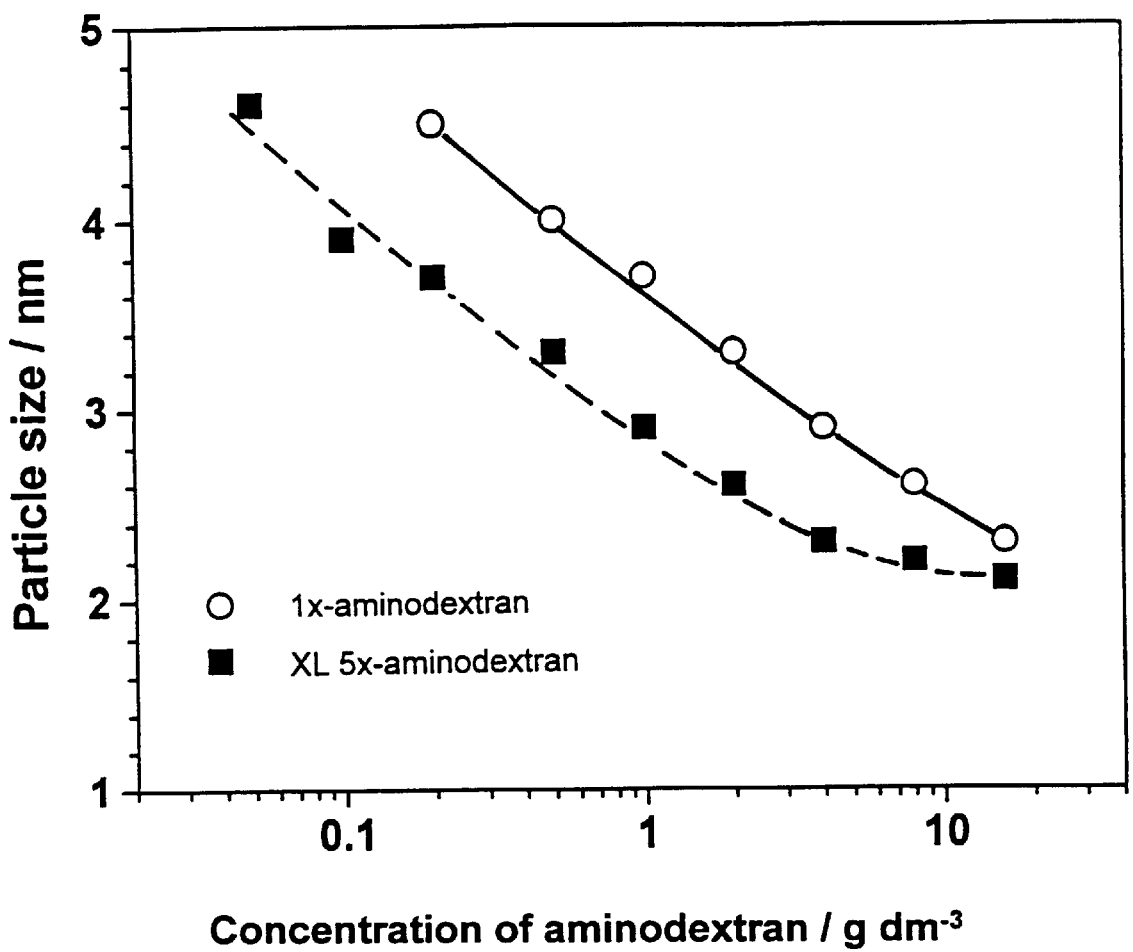
FIG. 12 is a plot of the mean diameter of CdS nanoparticles vs. concentrations of 1x-aminodextran and 5x-aminodextran, lot 2-2.

The behavior of the 5x-aminodextran, lot 2-2 CdS dispersions is rather similar to that of 1x-aminodextran-CdS dispersions. FIG. 12 compares the mean diameters of CdS particles as a function of the concentration of 5x-aminodextran, lot 2—2 and 1x-aminodextran. Specifically, FIG. 12 shows that the mean diameter of CdS nanoparticles decreases as the concentrations of aminodextrans become higher.

Figure 13:
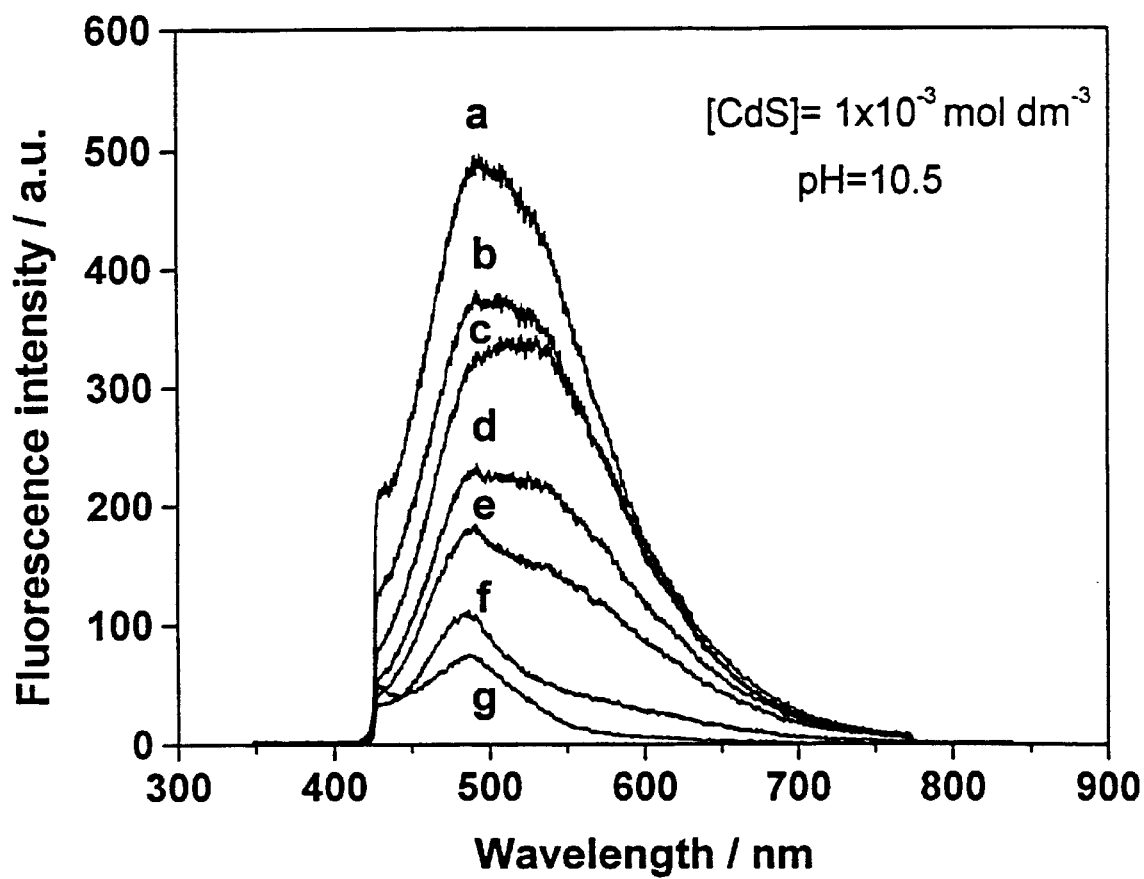
FIG. 13 provides luminescence spectra of CdS nanoparticles prepared with $3\times10^{-3}$ mol dm$^{-3}$(M) Cd(ClO$_4$)$_2$ and $2\times10^{-3}$ mol dm$^{-3}$(M) Na$_2$S solutions using different concentrations of 5x-aminodextran, lot 2—2 as a stabilizer: 16 (a), 8 (b), 4 (c), 2 (d), 1 (e), 0.5 (f), and 0.2 (g) g dm$^{-3}$.

The luminescence spectra of 5x-aminodextran, lot 2-2-CdS dispersions show a maximum at 490 nm for low Amdex concentrations, shifting to about 500 nm at the highest concentration, and maintaining a bandwidth of about 150 nm (FIG. 13).

Spectral features of all Amdex-CdS dispersions were placed on a relative basis by using the identical instrument settings (5 and 2.5 nm slits), excitation source, and fluorescence cell for all measurements. Amdex concentrations were 2.5, 5.0, 10, and 20 g dm$^{-3}$ while CdS concentrations were $5\times10^{-4}$, $1\times10^{-3}$, $5\times10^{-3}$, and $1\times10^{-2}$ M for most runs. 1x-aminodextran-CdS dispersions showed luminescence intensities increasing from about 40 to 90 in arbitrary units for the two lowest CdS concentrations. Little or no luminescence intensity was detected at CdS concentrations greater than $1\times10^{-3}$ M. 5x-aminodextran, lot 2-2-CdS dispersions had intensities ranging from 70 to 50 a.u. for the two lowest CdS concentrations, and <5 a.u. for concentrations greater than $1\times10^{-3}$ M. Luminescence bandwidths were narrower, about 100 nm, at lower Amdex concentrations. 5x-aminodextran, lot 11-6-CdS sols showed luminescence intensities at about 490 nm ranging from 100 to 75 a.u. for the lowest CdS concentration, and narrower luminescence bandwidths of 100 nm at all Amdex concentrations. Again, the highest two CdS concentrations gave luminescence intensities <5 a.u. at the maximum. 5x-aminodextran, lot 1-5-CdS sols showed luminescence intensities at 490 nm of about 80 to 130 a.u. for the lowest two CdS concentrations with narrower bandwidths of about 100 nm. Hydrosols at the higher two CdS concentrations all had maximum luminescence intensities below 15 a.u. Amdex-3M-CdS suspensions at the lowest CdS concentration showed luminescence intensities at maxima between 530 and 540 nm of 2 to 5 a.u., and bandwidths of about 100 nm. The sols prepared at higher CdS concentrations were mostly unstable, showing formation of a white precipitate which settled out within several hours. The average CdS particle size from the absorption onsets ranged from 3.2 to 4.1 nm. Amdex-3000-CdS dispersions gave luminescence intensities at band maxima between 450 and 510 nm of 20 to 190 a.u., and the narrowest bandwidths of 75 to 100 nm, for the two lowest CdS concentrations. Sols prepared at the two highest CdS concentrations were unstable or gave intensities <5 a.u. CdS nanoparticle diameters obtained from absorption onsets were very low, ranging from 2.4 to 1.9 nm for the lowest CdS concentration.

It is also instructive to use the above concentrations of aminodextran and cadmium sulfide particles to compare the numbers of CdS nanoparticles of 2.8 nm diameter per mL that would be formed in 200 mL of $1\times10^{-3}$M CdS against the number of 5x-Amdex, lot 1-5 molecules at 20 g dm$^{-3}$ in the same volume. For $2\times10^{-4}$ mol CdS (144.47 g mol$^{-1}$) with a bulk density of 4.50 g cm$^{-3}$ and volume of 11.49 nm$^3$ per nanoparticle, we obtain $2.8\times10^{-5}$ particles/mL. 5x-Amdex at 20 g dm$^{-3}$ and average MW of 34.4 kDa gives $3.5\times10^{17}$ molecules/mL. Thus, the ratio of nanoparticles-to-molecules of 5x-Amdex is about 1:100 at 20 g dm$^{-3}$; however, at 0.2 g dm$^{-3}$ of 5x-Amdex the ratio is about 1:1. Stabilities and luminescence intensities of aminodextran-CdS dispersions are much greater when they are prepared with excess polymer concentrations in the range, 1–20 g dm$^{-3}$.

The range of polymeric carrier, aminodextran, characteristics has been expanded to include a wide variety of aminodextrans. Of the aminodextrans used in CdS nanoparticle preparations at 20 g dm$^{-3}$, the order of increasing total amine concentration was:
Amdex-3M [$8.7\times10^{-4}$M]<Amdex-3000 [$1.1\times10^{-2}$ M]<1X-Amdex [$1.2\times10^{-2}$ M]<5X-Amdex, lot 2-2 [$8.2\times10^{-2}$ M]~5X-Amdex, lot 11-6 [$8.2\times10^{-2}$ M]<5X-Amdex, lot 1-5 [$9.8\times10^{-2}$ M]. The concentrations of total amine (primary and secondary) in each 20 g dm$^{-3}$ aminodextran solution were calculated from data shown in Table 3.

TABLE 3

Amine substitution data for aminodextrans.

| | MW, Kda | Glucose units per molecule | Degree of subst | Mol diaminopropane per mol Amdex | Mol amine per mol Amdex |
|---|---|---|---|---|---|
| 5X-Amdex, lot 1-5 | 34 | 209.7 | 2/5 | 83.9 | 167.8 |
| 5X-Amdex, lot 11-6 | 44.5 | 274.5 | 1/3 | 91.4 | 182.8 |
| 5X-Amdex, lot 2-2 | 168.4 | 1038.9 | 1/3 | 345.9 | 691.8 |
| 1X-Amdex | 93 | 573.7 | 1/20 | 28.7 | 57.4 |
| Amdex-3M | 3,000 | 18,507 | 1/142 | | 130 |
| Amdex-3000 | 3 | 18.5 | 1/11 | | 1.7 |

The order of increasing luminescence emission intensity was: Amdex-3M [about 3–4]<5X-Amdex, lot 2-2 [50]<5X-Amdex, lot 11-6 [about 60–80]<1X-Amdex, [about 90]<5X-Amdex, lot 1-5 [about 90–120<Amdex-3000 [about 180–190]. Note that the 5X-Amdex lots are not aligned with the general trend of increasing luminescence emission with increasing total amine concentration; however, among lots of 5X-Amdex, the trend is maintained. The order by increasing size of Amdex in aqueous solution is: Amdex-3M [R=101.2 nm diameter]>5X-Amdex, lot 2-2 [25.3 nm]>1X-Amdex [21.5 nm]>5X-Amdex, lot 11-6 [13.2 nm]>5X-Amdex, lot 1-5 [12.1 nm]>Amdex-3000. Note that the smallest aminodextrans by size have yielded CdS-aminodextran conjugates with the most intense luminescence emission. Also, the largest CdS-Amdex nanoparticles showed the least luminescence intensity since the largest Amdex (3M Da) had the fewest amino groups (1/142 degree of substitution) and the lowest amine concentration.

It should be noted, that it was not possible to prepare luminescent CdS nanoparticles using dextrans, but strong luminescence could be achieved with aminodextrans, depending on their concentration in the reaction mixture. This finding suggests that the presence of amino groups in the dextran molecules and a high pH medium are essential for the activation of CdS nanoparticle luminescence. The higher luminescence intensity of particles prepared with 5x-aminodextran, lot 2-2 than of those obtained with 1x-aminodextran, is most likely caused by the difference in the degree of substitution of these two polymers. The obvious question is how amino-groups enhance the luminescence intensity. Previous studies have reported strong sensitivity of the luminescence quantum yield to chemical modification of the cluster surface [Fojtik, A., Weller, H., Koch, U., and Henglein, A., Ber. Bunsenges. Phys. Chem. 88, 969 (1984); Rossetti, R., et al., J. Chem. Phys. 80, 4464

(1984)]. The wurtzite or zinc blende crystalline structures of CdS nanocrystals leave surface cadmium atoms with fewer bonds to nearest neighbors of sulfur atoms, three instead of the usual four in the interior of the nanocrystal. It is known that the semiconductor nanoparticles have a high density of surface defect sites, which cover a broad range of energies [Fojtik, A., cited above; Henglein, cited above; Nozik, A., J. Phys. Chem. 90, 12 (1986)]. Most of such sites exist in the midband gap energies and are involved in trapping initially produced electron-hole pairs.

The investigation of Dannhauser and co-workers has shown that several tertiary amines significantly enhance luminescence intensity, when added to a suspension of CdS nanoparticles [Dannhauser, T. et al., J. Phys. Chem., 90, 6074 (1986)]. This effect was interpreted as due to the modification of midband gap states, probably associated with $Cd^{2+}$ binding to amines. The latter raises the site energy, effectively removing these sites as efficient traps, thus increasing luminescence intensity.

Enhanced luminescence emission intensity from CdS nanoparticles was achieved by forming multiple nanoparticles in the domain of single polymer molecules of aminodextran. The nanoparticles of diameter 2–3 nm are substantially smaller than the 5x-aminodextran, R=9.28 to 25.3 nm and MW=25.6 to 168.4 Da, that was used subsequently in conjugations of monoclonal antibody. Thus, it is possible for more than one nanoparticle to be attached to a single molecule of 5x-aminodextran. This is similar to the conjugation of multiple numbers of phycoerythrin(PE) molecules together with monoclonal antibody to aminodextran, as described previously. PE is monodisperse with a molecular weight of 270,000 Da and a diameter of 27.7 nm. CdS nanoparticles can be similarly characterized. The number of atoms per particle of CdS is estimated from the volume per spherical particle of 2.8 nm diameter as 11.49 $nm^3$ divided by the volume of a unit cell (0.5975 nm edge for cubic cell) occupied by four CdS units or 8 atoms as 0.2133 $nm^3$. The quotient (11.49 $nm^3$ //0.2133 $nm^3$/8 atoms) yields 431 atoms. Since one-half of the atoms are cadmium and one-half, are sulfur, the molecular weight of a 2.8 nm diameter CdS particle is estimated as (215×112.41+215×32.06)=31,000 Da. The density of bulk CdS in the zinc blende structure is 4.50 g/cc, at least 4-fold larger than the density of a typical organic polymer; thus, the size of CdS particles is proportionally smaller than typical 5x-aminodextrans.

The main criteria for success in obtaining optimal yields of CdS nanoparticles with aminodextran, that produce large luminescence intensities and have reasonable stability to activating reagents appear to be the following: 1. high aminodextran concentration; 2. high concentration of amine (primary and secondary) groups in aminodextran; 3. high molecular weight of aminodextran; 4. excess Cd(II) ion concentration; 5. high pH.

The present experiments have demonstrated that the interaction between nanocrystal surfaces and the aminodextran can be controlled through changing the degree of substitution of amine groups in the aminodextran molecule, which makes it possible to tailor the size, stability, and optical properties of CdS dispersions by the choice of the composition and the concentrations of these polymers.

EXAMPLE 5

Preparation of ZnS Nanoparticles by the CDJP Process

In a CDJP process, 50 $cm^3$ of zinc sulfate ($ZnSO_4$) and sodium sulfide ($Na_2S$) solutions were separately and simultaneously introduced at the constant flow rate of 10 $cm^3$ $min^{-1}$ into 100 $cm^3$ of an aqueous solution, containing 5x-aminodextran as the stabilizing agent. The dispersion was agitated with a stirrer at 700 rpm. All experiments were carried out at the constant temperature of 25° C.

The concentration of the reactants, i.e., zinc salt and sodium sulfide, was varied from $1\times10^{-3}$ M to $1\times10^{-2}$ M, while the molar ratio was kept constant at $[Zn^{2+}]/[S^{2-}]=1$. The concentration of 5x-aminodextran in the system was constant at 5 g $dm^{-3}$. In changing the concentration of these solutions the ionic strength was varied, which may have affected the particle size. A summary of the precipitation conditions that were used in the formation of ZnS dispersions is given in Table 4.

TABLE 4

Conditions for the preparation of nanosized ZnS particles by the CDJP process in the presence of 5 g $dm^{-3}$ 5x-aminodextran.

| sample | $[Zn^{2+}]$ & $[S^{2-}]$ M | pH | color | absorption onset nm | bandgap eV |
|---|---|---|---|---|---|
| a | 0.001 | 9.2 | colorless | 290 | 4.28 |
| b | 0.005 | 8.6 | colorless | 299 | 4.15 |
| c | 0.01 | 8.3 | colorless | 306 | 4.05 |

The precipitation of zinc sulfide by the CDJP process in the presence of 5x-aminodextran resulted in stable dispersions of nanosized particles. The difference in the particle size can be recognized from the onset of the absorption, which shows the dependence of the particle size on the concentration of the reactants. The onset of the absorption determined from $5\times10^{-4}$ M ZnS dispersions shifted from 290 nm (sample a) to 306 nm (sample c). These results correspond to quantum energies larger than that of ZnS as macroscopic solid (3.67 eV), indicating the formation of quantized ZnS nanoparticles. The bandgaps are somewhat larger in energy than those reported in the literature [Henglein, A. et al., Ber. Bunsenges. Phys. Chem. 87, 852–858 (1983); Weller, H. et al., Ber. Bunsenges. Phys. Chem. 88, 649–656 (1984); Dunstan, D. E. et al., J. Phys. Chem. 94, 6797–6804 (1990); Qi, L. et al., Colloids Surfaces 111, 195–202 (1996)], indicating the formation of extremely small quantized ZnS nanoparticles. Thus, 5x-aminodextran provides a good medium for preparation of nanosized ZnS particles by the CDJP process.

EXAMPLE 6

Preparation of Mixed CdS-ZnS Nanoparticles

Single CdS or ZnS nanoparticles were also prepared by rapid mixing of 50 $cm^3$ of $2\times10^{-3}$ M $CdSO_4$ or $ZnSO_4$ solutions with 50 $cm^3$ of $2\times10^{-3}$ M $Na_2S$ solution containing 5 g $dm^{-3}$ 5x-aminodextran. The final CdS or ZnS concentration was $1\times10^{-3}$ M.

The rapid mixing of 50 $cm^3$ of solution containing $CdSO_4$ and $ZnSO_4$ in a total concentration of $2\times10^{-3}$ M (but in different ratios) with 50 $cm^3$ of $2\times10^{-3}$ M $Na_2S$ solution led to the formation of mixed $Zn_xCd_{1-x}S$ nanoparticles. The final $Zn_xCd_{1-x}S$ concentration was $1\times10^{-3}$ M while x value was varied as determined by the molar ratio of $Cd^{2+}$ and $Zn^{2+}$ contained in the solution.

The chemical composition and some properties of these nanoparticles are given in Table 5.

TABLE 5

Characterization of mixed CdS-ZnS nanoparticles.

| sample | composition | pH | color | absorption onset nm | bandgap eV |
|---|---|---|---|---|---|
| a | ZnS | 9.0 | colorless | 294 | 4.22 |
| b | $Zn_{0.7}Cd_{0.3}S$ | 9.1 | colorless | 344 | 3.60 |
| c | $Zn_{0.5}Cd_{0.5}S$ | 9.3 | colorless | 375 | 3.31 |
| d | $Zn_{0.3}Cd_{0.7}S$ | 9.4 | pale yellow | 406 | 3.05 |
| e | CdS | 9.5 | yellow | 431 | 2.88 |

Single ZnS nanoparticles have an absorption onset at 294 nm, which corresponds to a bandgap of 4.22 eV, indicating the formation of extremely small quantized ZnS nanoparticles. Single CdS particles show an absorption onset at 431 nm, corresponding to an average particle size of <2.5 nm. Absorption spectra of $Zn_xCd_{1-x}S$ nanoparticles were found to lie between those of CdS and ZnS nanoparticles. Absorption onsets systematically shifted towards shorter wavelengths, from 431 nm to 294 nm, on increasing the amount of zinc in $Zn_xCd_{1-x}S$. Mixed nanoparticles show a continuously tunable energy gap from single CdS nanoparticles to single ZnS nanoparticles.

The absorption spectrum for the mixture of single CdS nanoparticles and single ZnS nanoparticles prepared separately with a Zn/Cd molar ratio of 1:1 shows two separate absorption edges, corresponding to those of single CdS and ZnS, which approximately reflects a superposition of CdS and ZnS spectra, unlike that of coprecipitated nanoparticles.

EXAMPLE 7

Metal Ion Coordination to Aminodextrans

Crucial to the formulation of any coherent picture of the mechanism of formation of CdS nanoparticles in the presence of aminodextran in an aqueous medium is the initial possibility of metal ion binding to sites on the aminodextran polymer. Towards this goal experiments were conducted to react chromophoric, aqueous copper(II) ions with aminodextran, using dextran as a control. Lot -26 1X-Amdex, which was analyzed as $C_{49}H_{84}O_{40}N.3H_2O$ with an empirical weight of 1,381.2 Da, was used. Thus, the molecular weight of the smallest repeating unit with two diaminopropane units substituted in one sugar ring is 5,525 Da. In one run, $2.000\times10^{-4}$ mol or 1.1 05 g of 1X-Amdex, lot -26 and the same amount of control, 1.105 g of dextran, T-2M, were separately dissolved in 50 mL of distilled water. To each sample were then added, stepwise, $2.00\times10^{-3}$ mol or 0.328 g of sodium acetate dissolved in 10 mL of distilled water, followed by $2.00\times10^{-3}$ mol or 0.465 g of $Cu(NO_3)_2.5/2H_2O$ dissolved in 25 mL of distilled water. The total volume of each sample was adjusted to 100 mL with distilled water, and the mixtures were stirred magnetically for 3 days. The mixture of Cu(II)-dextran became cloudy and was filtered through an 0.45 micron filter before measuring its electronic absorption spectrum in the visible-to-near-UV region. After the mixing period, the Cu(II)-dextran sample gave pH=5.31, conductivity=6.05 mmho-cm$^{-1}$, $\lambda_{max}$=771 nm, and $A_{771}$=0.453, while the Cu(II)-1X-Amdex sample gave pH=5.79, conductivity=5.68 mmho-cm$^{-1}$, $\lambda_{max}$=747 nm, and $A_{747}$=0.534. Both samples were then separately washed with distilled water by membrane filtration (A/G Technology Corp. Model UFP-30-E-4 hollow fiber cartridge, 30,000 Da MW cut-off) to remove excess salts. After washing, the colorless Cu(II)-dextran sample gave pH=6.53, conductivity=4.25 ,mho-cm-1, and no detectable absorbance greater than 0.007 units between 400 and 900 nm; whereas, the distinctly blue Cu(II)-1X-Amdex sample gave pH=6.32, conductivity=4.05 $\mu$mho-cm$^{-1}$, $\lambda_{max}$=630 nm, and $A_{630}$=0.050. Assuming that the weak absorption bands originating from d-d transitions of the Cu(II) species before and after washing have not changed much in their molar extinction coefficients, then the approximately 10% remaining absorbance matches the amount of Cu(II) needed to exactly occupy all the doubly diaminopropane-substituted sugar sites of 1X-Amdex. All of the Cu(II)-1X-Amdex sample was freeze-dried to provide 0.765 g of dried solid, so that the molar extinction coefficient of the 630 nm absorption band was calculated to be about 35 dm$^3$-cm/mol. Elemental analyses of the solid, 0.56% N and 0.54% Cu, showed that 85% of the 4N sites of doubly diaminopropane-substituted glucose residues were occupied by Cu(II). Molecular models of these DAP-substituted residues have shown that four-coordination of Cu(II) to the four nitrogen electron-pair-donor atoms of two diaminopropane units substituted on the same glucose residue of dextran is sterically feasible. The two six-membered chelate rings comprising of $Cu(NH_2CH_2CH_2CH_2N)_2$— are consistent with known coordination chemistry of stable transition metal chelates. Intramolecular or intermolecular Cu(II) crosslinks between two diaminopropane units on different glucose residues are less favorable sterically. Similar binding of other divalent transition metal ions such as Zn(II) and Cd(II) is expected. The selectivity of 1X-Amdex for Cu(II) ions was shown with the same amounts of 1X-Amdex and Cu(II) as above, but in the presence of a 50-fold excess of Zn(II) ions from $Zn(NO_3)_2.6H_2O$. The mixture was stirred overnight and then washed by membrane filtration to give a faint blue solution, pH 6.75, conductivity 4.15 1$\mu$mho-cm$^{-1}$, $\lambda_{max}$=618 nm, and $A_{618}$=0.038. Comparison against absorbance when only Cu(II) was present gave 79% Cu(II) incorporation in the presence of excess Zn(II). Being in the same group IIB in the periodic table, cadmium(II) is expected to bind to aminodextrans in a similar way to Zn(II).

EXAMPLE 8

Preparation of T4 Antibody-5X-Amdex-CdS Conjugate

Coulter T4 monoclonal antibody, CD4 clone SFCI12T4D11 (IgG1), was derived from hybridization of mouse NS/1-AG4 cells with spleen cells of BALB/cJ mice immunized with peripheral human T lymphocytes (T4 antibody from Beckman Coulter, Inc., Miami, Fla.).

Emission and excitation spectra of T4–5X-Amdex-CdS conjugates were measured with a Shimadzu Model RF5000U spectrofluorimeter using a xenon lamp for excitation. Quasi-elastic light scattering, QELS (or photon correlation spectroscopy, PCS) and its analysis were obtained with a COULTER Model N4MD sub-micron particle analyzer with size distribution processor (SDP) analysis and multiple scattering angle detection with 632.88 nm He/Ne laser excitation.

Standard primary amino functional group activation and conjugation procedures that are described in detail in the Pierce catalog [Pierce Catalog and Handbook, Life Science & Analytical Research Products, 1994/95, Pierce Chemical Company, Rockford, Ill.] and other monologs [Wong, S. S., Chemistry of Protein Conjugation and Cross-Linking (CRC Press, Inc., Boca Raton, Fla., 1991); Hermanson, G. T., Bioconjugate Techniques (Academic Press, San Diego, Calif., 1996); Aslam, M. and Dent, A., Bioconjugation- Protein Coupling Techniques for the Biomedical Sciences (Grove's Dictionaries Inc., New York, N.Y., 1998)] were followed. Sulfosuccinimidyl 4-(N-maleimidomethyl) cyclohexane-1-carboxylate (sulfo-SMCC) was a Pierce product while 2-iminothiolane, L-cysteine free base, and iodoacetamide were Sigma grade.

Figure 14:
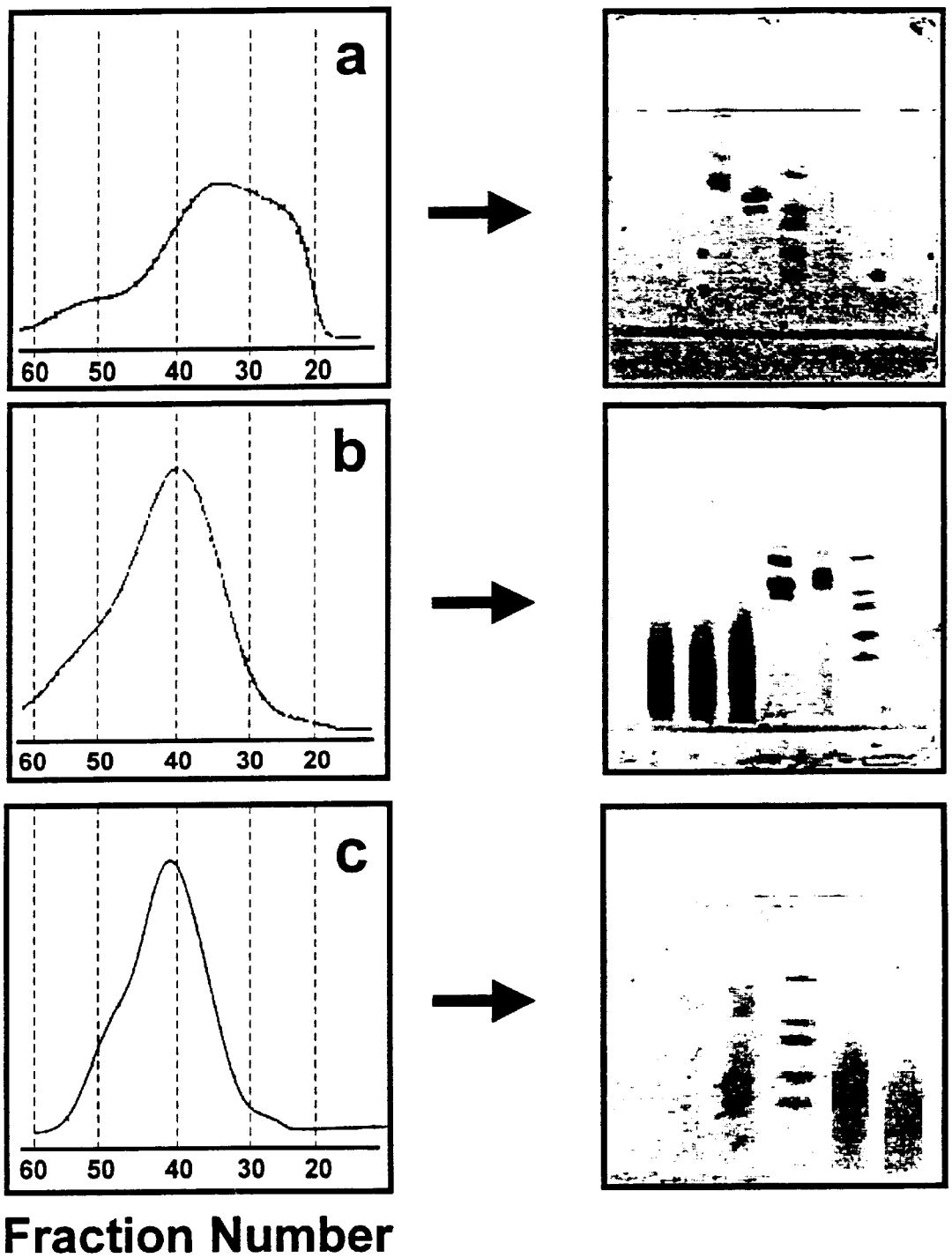
FIGS. 14A–14C show the $A_{280}$ monitor reading versus fraction number chromatogram on Bio-Gel A-5m for T4-5X-Amdex-CdS conjugation mixtures: A, run 7; B; run 9; C, run 10. On the RHS are SDS-PAGE results as follows: A, lane 1, pooled fractions 22–30; lane 2, pooled fractions 31–40; lane 3, purified T4 antibody; standards; B, lanes 1–3, successive fractions of 5X-Amdex-CdS complex purified on Sephadex G-25; lane 4, IT-T4 antibody; lane 5, pooled fractions 31–40; lane 6, standards; C, lane 4, standards; lanes 1, 2, 3, 5, and 6 are pooled fractions 31–35, 36–40, 41–45, 46–50, and 51–55, respectively.

In Run 7, ten milliliters of raw 5X-Amdex-CdS dispersion, prepared at a 20 g dm$^{-3}$ 5X-Amdex, lot 1-5 concentration, were purified and buffer exchanged on a 2.5 cm×48 cm G-25 Sephadex column equilibrated and eluted with 1×PBS, and collected in 120 drop (~3.6 mL) fractions. Two luminescent bands were observed with a 366 nm UV lamp, a narrow first band and a broader and brighter second band. Three of the brightest fractions(24–26) of the second band were combined into a 10.8 mL volume. 0.200 mL of sulfo-SMCC solution, 10 mg/mL in 1×PBS, were used for activation. The mixture was roller mixed for one hour, and then separated on a G-25 Sephadex column [Pharmacia Biotech], retaining the two brightest fractions (23 and 24) of 7.2 mL total volume. 25 mg of 47.16 mg/mL T4 antibody concentrate was activated with 0.161 mL of 2.0 mg/mL 2-iminothiolane solution in 1×PBS. 0.976 mL of 1×PBS buffer solution was added to the mixture, which was then roller mixed for one hour. The mixture was purified on G-50 Sephadex [Pharmacia Biotech], retaining the middle fraction of the first band, containing 4.5 mL of 3.831 mg/mL or 17.240 mg IT-T4. Conjugation of 7.2 mL of sulfo-SMCC-5X-Amdex-CdS suspension with 4.5 mL of IT-T4 solution was accomplished by roller mixing for two hours. The conjugation mixture was separated on a Bio-Gel A-5m column [Bio-Rad Laboratories], 2.5 cm×48 cm, equilibrated with 1×PBS. Two initial broad, poorly separated, bands (fractions 22–30, 32.4 mL and 31–40, 36.0 mL) were retained, and each pooled and concentrated in Amicon Centri-Prep 30 tubes by centrifugation for 20min at 200 rpm in an IEC Centra-8 centrifuge to 3.7 and 2.8 mL, respectively. Runs 9 and 10 were carried out in a similar way except 15 mL of raw 5X-Amdex-CdS sol were purified on G-25 Sephadex, 0.300 mL of 10 mg/mL sulfo-SMCC solution were used for activation, and the two brightest fractions (22 and 23) of sulfo-SMCC-5X-Amdex-CdS were pooled and mixed with 17.000 mg (5.229 mL) of IT-T4 in Run 9. Run 10 was similar to Run 9 except 0.400 mL of 10 mg/mL sulfo-SMCC solution was used and the four brightest fractions (21, 22, 23, and 24) of sulfo-SMCC-5X-Amdex-CdS were pooled and mixed with 17.900 mg (5.000 mL) of IT-T4. Traces of the UV monitor-recorder for fractions collected from the Bio-Gel A-5m column for Runs 7, 9, and 10 are shown in FIG. 14, together with SDS-PAGE results for specified, pooled fractions from each run.

Using the same level of activation of 5X-Amdex with sulfo-SMCC as in previous conjugations of 5X-Amdex with CD3 antibody [U.S. Pat. No. 5,527,713; U.S. Pat. No. 5,658,741] or with phycoerythrin and monoclonal antibody would require 0.450mL of 10 mg/mL sulfo-SMCC solution or 0.010 mmol sulfo-SMCC (MW, 436.37 g/mol) per 25 mg 5X-Amdex. For a two diaminopropane group repeating unit of 4×355.3 Da and 2 mol of primary amine per repeating unit, there would be 0.035 mmol of amine groups per 25 mg 5X-Amdex. Thus, the amine-to-sulfo-SMCC molar ratio was 3.5, providing enough sulfo-SMCC to activate about 30% of the primary amine groups in 5X-Amdex. In the present runs with 5X-Amdex-CdS conjugates best results were obtained at about 10-fold lower activation levels where the amine-to-sulfo-SMCC molar ratio was about 30 to 50, giving enough sulfo-SMCC to activate 2–3% of the primary amine groups in 5X-Amdex. Higher sulfo-SMCC amounts between 0.400 and 0.900 mL of 10 mg/mL sulfo-SMCC solution in the above procedure reduced the luminescence intensity of CdS nanoparticles by about 5–10-fold to very low levels. Higher IT-T4 amounts between 18 and 42 mg during conjugation simply gave more excess antibody in fractions 35 to 50 on the Bio-Gel A-5 column [Bio-Rad Laboratories], affording a poorer separation of conjugates from free antibody.

EXAMPLE 9

Spectral Measurements of Purified 5X-Amdex-CdS and T4 Antibody-5X-Amdex-CdS Conjugates Fifteen milliliters of raw sol were applied to the top of a G-25 Sephadex column (2.5 cm×48 cm) equilibrated with 1×PBS. Fractions of 120 drops or about 3.6 mL were collected. A narrow first band at about fraction no. 21 and a broader second band between fraction nos. 23 and 25 were observed with an $A_{280}$ monitor, as well as a hand-held lamp (366 nm, Model UVL-21 Blak-Ray lamp, Ultra-Violet Products, Inc., San Gabriel, Calif.) to observe luminescence emission on the column. Absorption spectra, luminescence emission spectra with 360 nm excitation, and QELS were measured for relevant fractions and the results are summarized in Table 6.

TABLE 6

Data for fractions of raw 5X-Amdex-CdS sol chromatographed on G-25 Sephadex.

| Fraction Number | Luminescence intensity, arbitrary units | 90° light scattering intensity, counts/sec × 10$^4$ | Mean diameter, nm |
|---|---|---|---|
| 20 | 214 | 2.34 | 4.5(3) |
| 21 | 255 | 6.91 | 4.4(3) |
| 22 | 586 | 8.79 | 4.7(3) |
| 23 | 980 | 8.35 | 7.0(3) |
| 24 | 910 | 6.33 | 9.2(3) |
| 25 | 840 | 4.29 | 10.4(2) |

Figure 15:
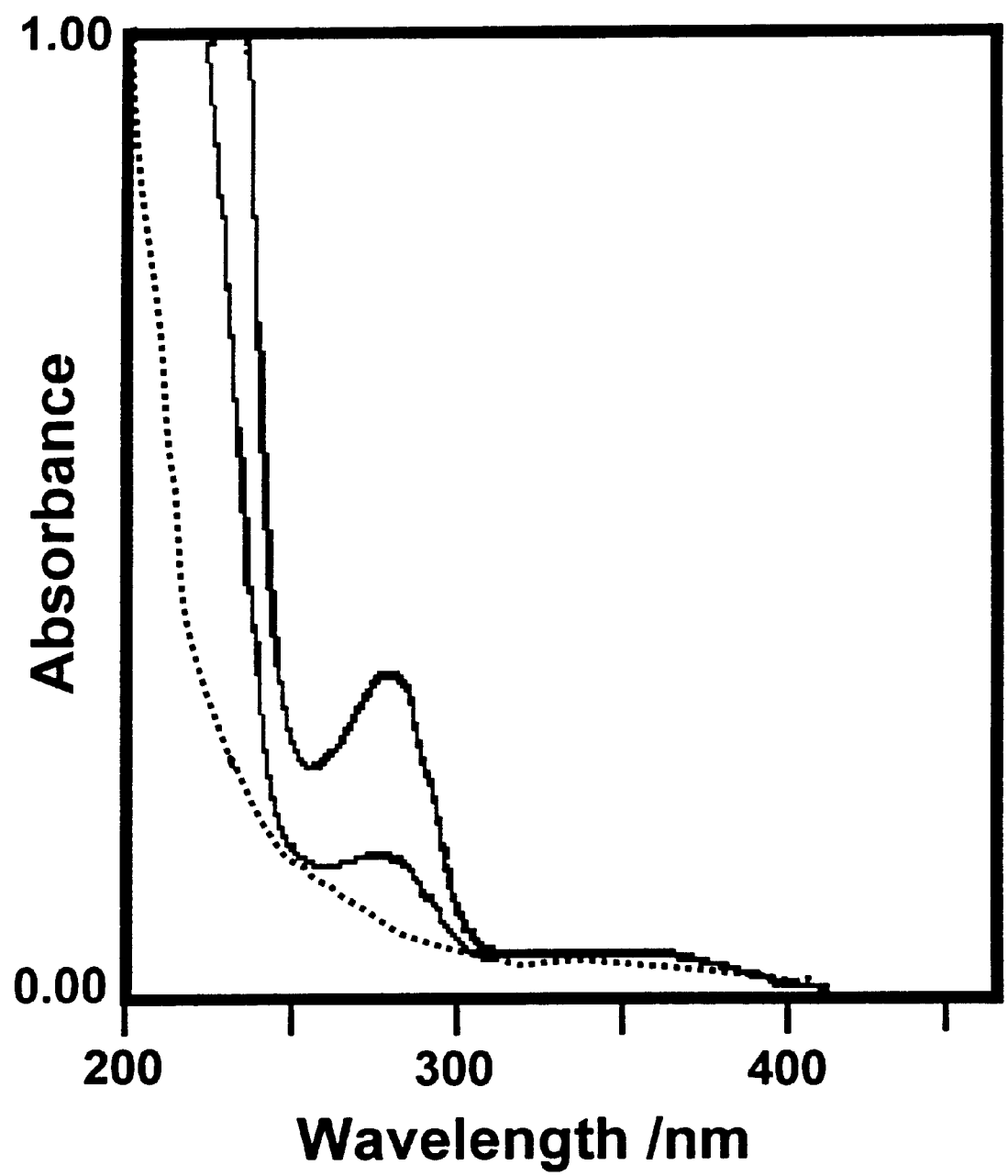
FIG. 15 shows the absorption spectra of T4–5X-Amdex-CdS conjugates in 1×PBS buffer solution: top, run 7, pooled and concentrated fractions 31–40; bottom, run 7, pooled and concentrated fractions 22–30.
Figure 16:
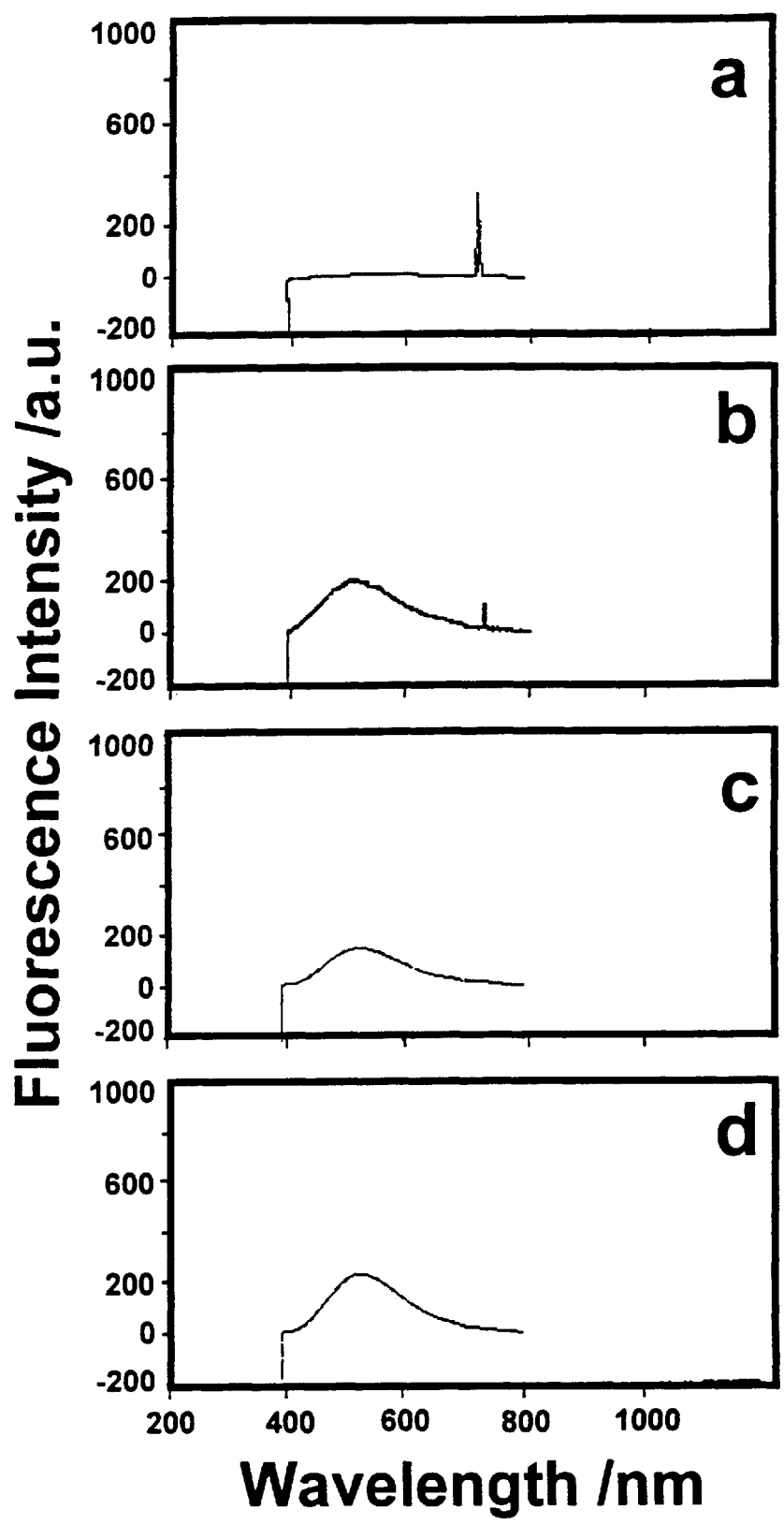
FIGS. 16A–16D show the luminescence emission spectra of T4–5X-Amdex-CdS conjugates in 1×PBS buffer solution with 360 nm excitation: A, run 7, pooled and concentrated fractions 22–30; B, run 9, pooled and concentrated fractions 31–40; C, run 10, pooled and concentrated fractions 31–45; and D, run 10, pooled and concentrated fractions 36–40.

The maximum absorption at about 365 nm was observed for fraction no. 21; however, maximum luminescence emission intensity was detected in three fractions, nos. 23–25, while maximum 90° light scattering occurred for fraction nos. 22 and 23. The T4–5X-Amdex-CdS conjugates showed an additional protein absorption band centered at 280 nm, as seen in FIG. 15 for run 7 samples. Further, the emission spectra of several runs of T4–5X-Amdex-CdS conjugates are compared with the same fluorimeter settings (1.5 nm excitation and emission slits) in FIG. 16. The highest of these emission band intensities at 500 nm was about 4- to 5-fold lower than the same band intensity for the parent 5X-Amdex-CdS complex, and for the fluorescent, organic dye, fura-2, pentapotassium salt (Molecular Probes, Inc.) at a concentration of 5 μM in 1×PBS buffer solution. QELS results for Run 7 conjugates, fractions 22–30 and fractions 31–40, were 32.7 nm and 24.3 nm, respectively, for the mean diameter from three measurements per sample. Using an average diameter of 9 nm for the 5X-Amdex-CdS raw sol fractions that were pooled, average thicknesses for the layer of T4 monoclonal antibody (IgG1 class) around the 5X-Amdex-CdS particles were calculated as 11.8 and 7.6 nm, respectively.

EXAMPLE 10

Biological Activity of T4-5X-Amdex-CdS Conjugates

Whole blood control (IMMUNO-TROL™, Beckman Coulter Inc., Miami, Fla.) was delivered in 100 μL volumes into 12×75 mm tubes. T4–5X-Amdex-CdS conjugate suspensions were added to respective tubes. Samples were processed with either digitonin or saponin (Sigma) in 1×PBS to provide a non-acid-lyse of red blood cells. Titers (10 to 50 μL) of T4–5X-Amdex-CdS conjugate were run to establish saturation of lymphocyte CD4 receptor sites. 500 4 μL of a 500 μg/mL digitonin or 0.1% saponin solution in 1×PBS was added, mixed, and incubated with sample mixtures in the tubes for 1 or 2 minutes, respectively. Cells were washed by adding 2 mL of PBSF (1×PBS with 0.01% sodium azide and 2.5% fetal bovine serum) to the tubes, centrifuged at 200 g for 5 minutes, supernatant solutions discarded, and 1 mL of PBSF added. Each run included a non-treated (no T4-5X-Amdex-CdS) control to establish fluorescence background for a negative gating region and a T4-5X-Amdex-CdS treated control to identify T4-5X-Amdex-CdS conjugate binding. The treated control was obtained by further incubating the mixtures in tubes with sheep anti-mouse antibody-phycoerythrin, SAM-PE (product of Silenus Laboratories, Hawthorne, Australia), for 15 min to identify the percent of cells with bound T4-5X-Amdex-CdS conjugate. The processed IMMUNO-TROL cells were analyzed on a COULTER® EPICS® Elite ESP™ flow cytometer. The cell suspensions were excited using an argon ion laser tuned to 488.0 nm with 100 mW output laser power. Fluorescence emission from PE or FITC was collected through an interference filter using a photomultiplier. Ten thousand events were collected for each sample after discriminating out electronic noise and debris. All sample data were collected and stored in list mode for further data reduction.

Figure 17:
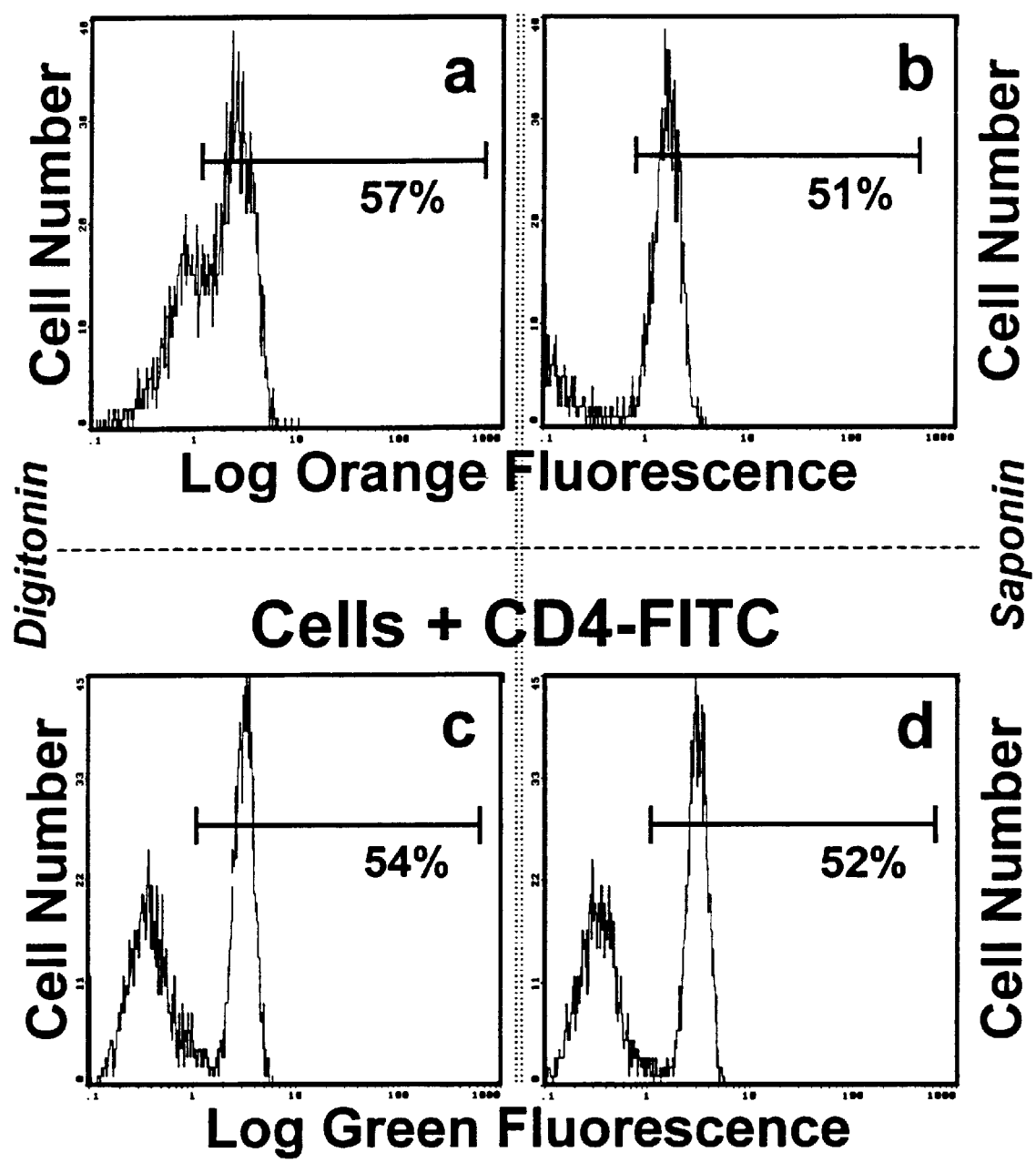
FIGS. 17A–17D show flow cytometry histograms, cell number (fluorescence events) versus log (fluorescence intensity) for T4-5X-Amdex-CdS conjugate/SAM-PE mixtures with whole blood control, lysed with either digitonin or saponin; and for direct labeling of T4+ cells in whole blood control with anti-CD4-FITC fluorescent marker.
Figure 18:
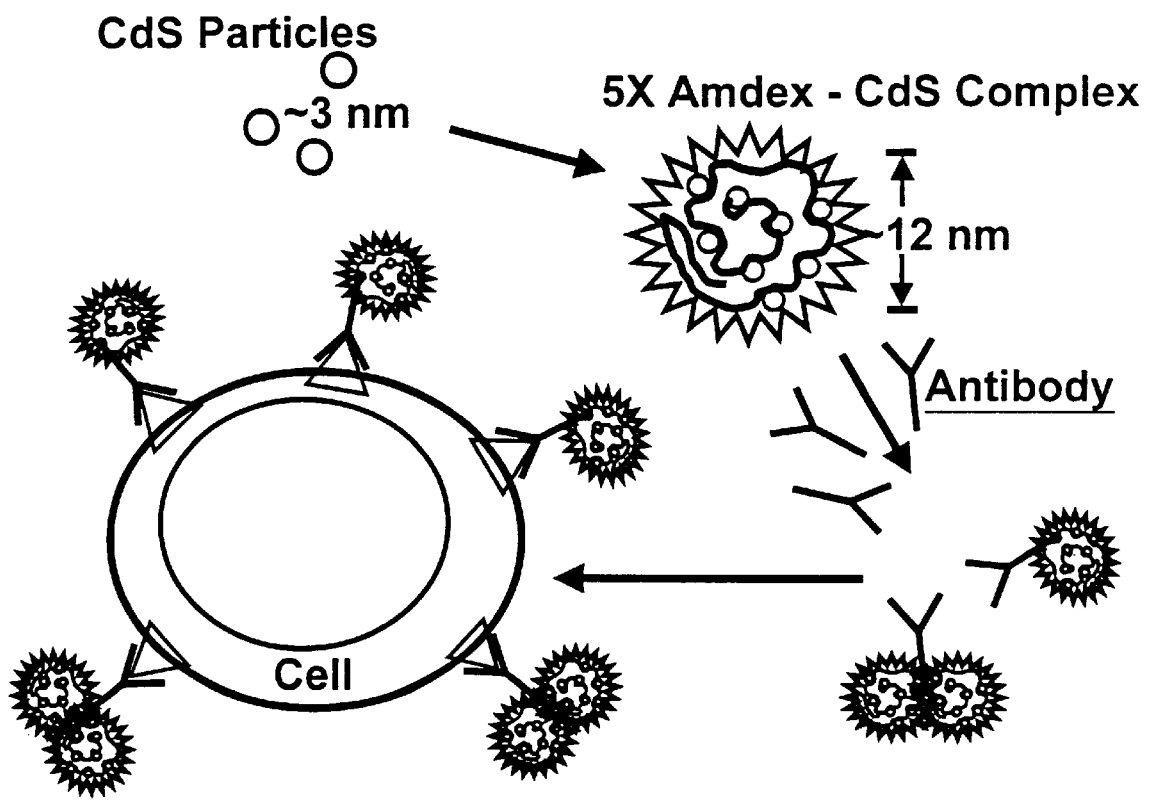
FIG. 18 gives a schematic illustration of the formation of T4-5X-Amdex-CdS conjugate and its binding to T4+ white blood cells.

Histograms obtained from flow cytometry of samples prepared as described for whole blood control mixed with T4-5X-Amdex-CdS conjugate/SAM-PE, and lysed with either digitonin or saponin are shown in FIG. 17, top half. Histograms of the same whole blood control treated with the direct marker, T4-FITC, only instead of T4–5X-Amdex-CdS/SAM-PE are shown in the bottom half of FIG. 17. Similar results for the percent T4 positive lymphocytes confirm that purified T4-5X-Amdex-CdS conjugate is labeling the same receptor sites on lymphocytes as the reference marker, T4-FITC. Thus, a model for the formation of the T4-5X-Amdex-CdS conjugate and its binding to T4+lymphocytes is displayed in FIG. 18.

The flow cytometry results show that it may not be possible to use all cadmium chalcogenide nanoparticles equally well as direct luminescence labels; rather, only CdSe and CdTe particles, which show band gap absorption band maxima in the visible and near-infrared spectral regions, have the potential to be readily used as direct markers. Luminescence emission intensities of CdS nanoparticles of 2–5 nm diameter attached to aminodextran of MW range, 30 to 75 kDa, and excited with near-UV laser lines were not high enough to be able to discriminate them from the high fluorescence background from white blood cells. Larger CdS nanoparticles of 5–10 nm diameter might be useful since their excitation bands are shifted into the visible region between 400 and 500 nm, wherein background luminescence intensities from white blood cells are not as high. Also, larger 5x-aminodextrans in the range 100 to 500 kDa have the potential to accommodate more CdS nanoparticles per molecule, and thus enhance luminescence intensities of these markers.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A method of detecting a target in a biological sample comprising the steps of:
    (a) contacting a biological sample suspecting of containing a target for a selected ligand with a ligand-semiconductor nanoparticle to form a bound ligand-semiconductor nanoparticle-biological sample, said ligand-semiconductor nanoparticle comprising the selected ligand having conjugated thereto at least one semiconductor nanoparticle, wherein said semiconductor nanoparticle comprises:
        (i) an amino derivative of a polysaccharide having a molecular weight from approximately 3,000 to 3,000,000 Da, a size in diameter of less than approximately 150 nanometers, and a degree of substitution of total number of primary and secondary amino groups in the polysaccharide molecule ranging from 1/150 to 4/1; and
        ii) at least one nanoparticle of the formula:

$$(X\ Y)_n$$

wherein X is selected from the group comprising $Cd^{2+}$, $Hg^{2+}$, and $Zn^{2+}$ and combinations thereof, and Y is selected from the group comprising $S^{2-}$, $Se^{2-}$ and $Te^{2-}$ and combinations thereof, and n=approximately 50 to 1000, wherein said nanoparticle is linked to said aminopolysaccharide;
    (b) exciting said bound semiconductor nanoparticle-biological sample with infrared to ultraviolet light to cause it to luminesce; and
    (c) detecting the luminescence signal, thereby detecting the presence of the target for a selected ligand in the biological sample.

2. The method according to claim 1, wherein the luminescent signal is measured by flow cytometric analysis.

3. The method according to claim 1, wherein the biological sample comprises white blood cells.

4. The method according to claim 1, wherein the ligand is an antibody or a functional fragment thereof.

5. The method according to claim 4, wherein the ligand is an anti-CD4 antibody.

* * * * *